United States Patent
Kim et al.

(10) Patent No.: US 7,191,004 B2
(45) Date of Patent: Mar. 13, 2007

(54) CAPTURE VERIFICATION USING AN EVOKED RESPONSE REFERENCE

(75) Inventors: Jaeho Kim, Redmond, WA (US); Joseph Bocek, Seattle, WA (US)

(73) Assignee: Cardiac Pacemakers, Inc., St. Paul, MN (US)

(*) Notice: Subject to any disclaimer, the term of this patent is extended or adjusted under 35 U.S.C. 154(b) by 500 days.

(21) Appl. No.: 10/335,599

(22) Filed: Dec. 31, 2002

(65) Prior Publication Data

US 2004/0127950 A1    Jul. 1, 2004

(51) Int. Cl.
*A61N 1/37* (2006.01)
*A61N 1/372* (2006.01)
*A61B 5/04* (2006.01)

(52) U.S. Cl. .................. 607/27; 607/28; 600/509

(58) Field of Classification Search ............ 607/27, 607/28; 600/517, 521
See application file for complete search history.

(56) References Cited

U.S. PATENT DOCUMENTS

| | | | |
|---|---|---|---|
| 4,825,869 A | 5/1989 | Sasmor | |
| 5,350,410 A | 9/1994 | Kleks et al. | 607/28 |
| 5,873,898 A * | 2/1999 | Hemming et al. | 607/28 |
| 6,038,474 A | 3/2000 | Zhu et al. | 607/9 |
| 6,101,416 A | 8/2000 | Sloman | 607/28 |
| 6,163,724 A | 12/2000 | Hemming et al. | 607/28 |
| 6,175,766 B1 | 1/2001 | Bornzin et al. | 607/28 |
| 6,275,731 B1 | 8/2001 | Zhu et al. | 607/9 |
| 6,418,343 B1 | 7/2002 | Zhang et al. | 607/9 |
| 6,731,985 B2 * | 5/2004 | Poore | 607/28 |
| 2003/0050671 A1 * | 3/2003 | Bradley | 607/27 |
| 2004/0127949 A1 | 7/2004 | Kim et al. | 607/27 |

* cited by examiner

*Primary Examiner*—Robert E. Pezzulo
*Assistant Examiner*—Tammie K. Heller
(74) *Attorney, Agent, or Firm*—Hollingsworth & Funk, LLC

(57) ABSTRACT

A method and system for verifying capture in the heart involves the use of pacing artifact templates. One or more pacing artifact templates characterizing a post pace artifact signal associated with a particular pace voltage or range of voltages are provided. A pacing artifact template is canceled from a cardiac signal sensed following a pacing pulse. Capture is detected by comparing the pacing artifact canceled cardiac signal to an evoked response reference. Fusion/pseudofusion detection involves determining a correlation between a captured response template and a sensed cardiac signal.

64 Claims, 16 Drawing Sheets

CAPTURE VERIFICATION USING AN EVOKED RESPONSE REFERENCE

FIELD OF THE INVENTION

The present invention relates generally to implantable medical devices and, more particularly, to verifying capture of the heart following the delivery of a pace pulse.

BACKGROUND OF THE INVENTION

When functioning normally, the heart produces rhythmic contractions and is capable of pumping blood throughout the body. However, due to disease or injury, the heart rhythm may become irregular resulting in diminished blood circulation. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contractile response in heart tissue, the contractile response is typically referred to as capture, and the electrical cardiac signal corresponding to capture is denoted the evoked response. Superimposed with the evoked response may be a pacing artifact signal including, for example, the signal associated with post pace residual polarization. The magnitude of the pacing artifact signal may be affected by a variety of factors including lead polarization, after potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart resulting in ineffective pacing. If the pace pulse energy is too high, the result may be patient discomfort as well as shorter battery life.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

A fusion beat is a cardiac contraction that occurs when two intrinsic cardiac depolarizations of a particular chamber, but from separate initiation sites, merge. When the heart is being paced, a fusion beat may occur when an intrinsic cardiac depolarization of a particular chamber merges with a pacer output pulse within that chamber. Fusion beats, as seen on electrocardiographic recordings, exhibit various morphologies. The merging depolarizations of a fusion beat do not contribute evenly to the total depolarization.

Pseudofusion occurs when a pacer output pulse artifact is superimposed upon a spontaneous P wave during atrial pacing, or upon a spontaneous QRS complex during ventricular pacing. In pseudofusion, the pacing stimulus is ineffective because the tissue around the electrode has already spontaneously depolarized and is in its refractory period.

During normal pacing, the presence of fusion and pseudofusion beats may be of little consequence except for wasted energy due to the generation of unnecessary pace pulses. However, detection of fusion and pseudofusion beats may be required during an automatic capture or threshold determination procedures. Fusion and pseudofusion beats may cause false detection of capture and may lead to erroneous capture threshold values.

Capture may be verified by detecting if a cardiac signal following a pace pulse indicates an evoked response. However, the evoked response must be discerned from the superimposed post pace residual polarization, denoted herein as a pacing artifact. In addition, fusion or pseudofusion beats may further obscure evidence of capture. It is desirable to detect the evoked response and thereby verify capture so that an effective pace pulse energy may be chosen and appropriate back up pacing delivered. For the reasons stated above, and for other reasons stated below which will become apparent to those skilled in the art upon reading the present specification, there is a need in the art for a method and device that reliably and accurately detects capture in a patient's heart by sensing an evoked response in the presence of the post pace residual polarization and possible fusion or pseudofusion beats. There exists a further need for such an approach that is adaptive and accommodates changes in the patient's capture threshold over time. The present invention fulfills these and other needs.

SUMMARY OF THE INVENTION

The present invention is directed to a method and device for verifying capture in the heart by comparing an evoked cardiac response with an evoked response reference. In accordance with one embodiment of the present invention, one or more pacing artifact templates are provided that characterize a pacing artifact signal associated with various pace voltage levels. An evoked response reference is determined. A cardiac signal is sensed following a pace pulse and a particular pacing artifact template is canceled from the cardiac signal. Capture is determined by comparing the pacing artifact canceled cardiac signal and the evoked response reference.

Another embodiment of the invention involves a method for detecting a fusion/pseudofusion cardiac beat. According to this embodiment, a captured response template is provided. The fusion/pseudofusion beat is detected by comparing a sensed cardiac signal to the captured response template.

Yet another embodiment of the invention involves a medical device for detecting capture in a patient's heart. The medical device includes a lead system extending into the heart including electrodes for stimulating and/or sensing the heart. Pulse generator circuitry is coupled to the lead system and is configured to generate pulses to stimulate the heart. Sensing circuitry is coupled to the lead system and is configured to sense cardiac signals transmitted through the lead electrodes. A control system controls operation of the device, including the pulse generator circuitry and the sensing circuitry. A capture detection system is coupled to the sensing circuitry and the control system. The capture detection system is configured to provide a pacing artifact template associated with a post pace signal and to determine an evoked response reference indicative of capture of the heart. The capture detection system cancels the pacing artifact template from cardiac signals sensed following a pulse, and detects capture of the heart by comparing the pacing artifact canceled cardiac signals and the evoked response reference.

A further embodiment of the invention involves a medical device for detection of fusion/pseudofusion beats. The medical device includes a lead system comprising electrodes and extending into the heart. Pulse generator circuitry is coupled to the lead system and is configured to generate pulses to stimulate the heart. Sensing circuitry is coupled to the lead system and is configured to sense cardiac signals transmitted through the lead electrodes. A control system controls operation of the device, including the pulse generator circuitry and the sensing circuitry. A fusion/pseudofusion detection system is coupled to the sensing circuitry and the control system. The fusion/pseudofusion system is configured to determine a captured response template and to detect fusion-lpseudofusion beats by comparing the sensed cardiac signals and the captured response template.

In accordance with another embodiment of the invention, a system for detecting capture of a patient's heart includes means for providing a pacing artifact template, the pacing artifact template characterizing a pacing artifact signal. The system further includes means for providing an evoked response reference, the evoked response reference indicative of capture of the heart, means for canceling the pacing artifact template from a cardiac signal sensed following a pacing pulse, and means for detecting capture of the heart by comparing the pacing artifact canceled cardiac signal and the evoked response reference.

In accordance with yet another embodiment of the invention, a system for detecting a fusion/pseudofusion beat includes means for determining a captured response template, means for sensing a cardiac signal, and means for detecting the fusion/pseudofusion beat by comparing the sensed cardiac signal and the captured response template.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
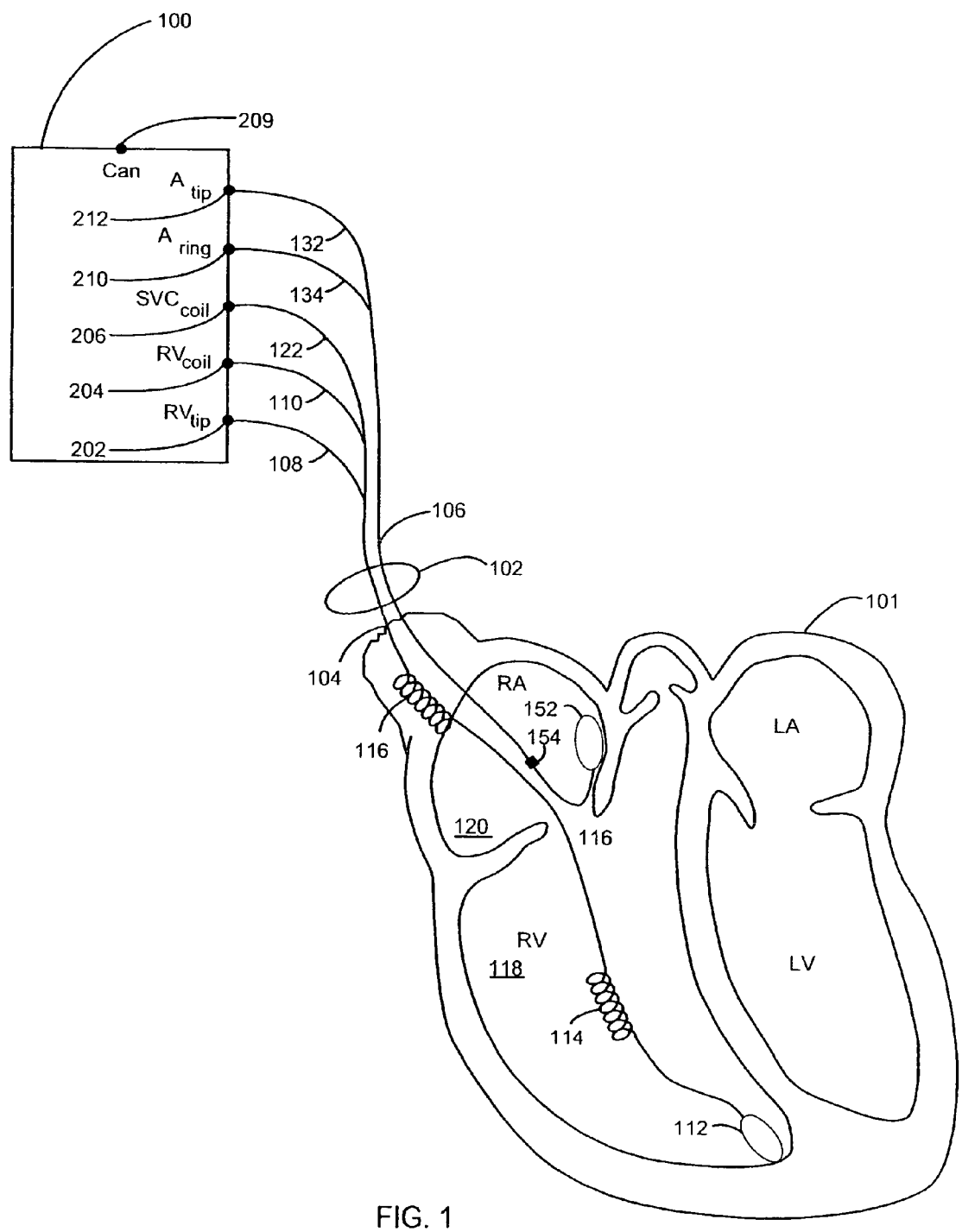
FIG. 1 is a partial view of one embodiment of an implantable medical device with an endocardial lead system extending into atrial and ventricular chambers of a heart.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

The present invention describes methods and systems for verifying capture following the application of a pace pulse to the heart. In accordance with various aspects of the invention, capture verification may be implemented by comparing a cardiac signal following the pace pulse to a template, or other reference, representative of an evoked response. Furthermore, fusion and/or pseudofusion detection may also be implemented using the principles of the invention.

By way of example, the processes of the present invention may be used to enhance capture verification and determination of the optimal energy for pacing. Determination of the optimal pacing energy may be implemented, for example, by an automatic capture threshold procedure executed by an implantable cardiac rhythm management system. Additionally, automatic capture verification may be used to monitor pacing on a beat-by-beat basis and to control back up pacing when a pace pulse delivered to the heart fails to evoke a contractile response. These and other applications may be enhanced by employment of the systems and methods of the present invention.

Those skilled in the art will appreciate that reference to a capture threshold procedure indicates a method of measuring the stimulation threshold in either an atrium or a ventricle. In such a procedure, the pacemaker, automatically or upon command, initiates a search for the capture threshold of the chamber. In one example of an automatic capture threshold procedure, the pacemaker automatically decreases the pulse amplitude in discrete steps until a predetermined number of consecutive loss-of-capture events occur. At that point, the pacemaker may increase the stimulation voltage in discrete steps until a predetermined number of capture events occur to confirm the capture threshold. Various methods of implementing capture threshold procedures are known in the art and may be enhanced by the capture detection methods of the present invention.

Automatic capture threshold determination is distinguishable from automatic capture detection, which is a procedure that occurs on a beat-by-beat basis. Automatic capture detection confirms on a beat-by-beat basis that a delivered pace pulse results in an evoked response. When no evoked response is detected following a pace pulse, the pacemaker may deliver a back up safety pulse to ensure consistent pacing. If a predetermined number of pace pulses delivered during normal pacing do not produce an evoked response, the pacemaker may initiate a capture threshold test as described above. The various procedures for implementing automatic capture detection and/or back up pacing processes may be enhanced by the capture detection methods described herein.

The embodiments of the present system illustrated herein are generally described as being implemented in an implantable cardiac defibrillator (ICD) that may operate in numerous pacing modes known in the art. Various types of single and multiple chamber implantable cardiac defibrillators are known in the art and may implement a capture verification methodology of the present invention. Furthermore, the systems and methods of the present invention may also be implemented in a variety of cardiac rhythm management systems, including single and multi chamber pacemakers, resynchronizers, and cardioverter/monitor systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Referring now to FIG. 1 of the drawings, there is shown one embodiment of a cardiac rhythm management system that includes an implantable cardiac defibrillator 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electrical cardiac signals produced by the heart 101 and to provide electrical energy to the heart 101 under certain predetermined conditions to treat cardiac arrhythmias, including, for example, ventricular fibrillation of the heart 101.

The intracardiac lead system 102 includes one or more pacing electrodes and one or more intracardiac defibrillation electrodes. In the particular embodiment shown in FIG. 1, the intracardiac lead system 102 includes a ventricular lead system 104 and an atrial lead system 106. The ventricular lead system 104 includes an SVC-coil 116, an RV-coil 114, and an RV-tip electrode 112. The RV-coil 114, which may alternatively be an RV-ring electrode, is spaced apart from the RV-tip electrode 112, which is a pacing electrode. In one embodiment, the ventricular lead system 104 is configured as an integrated bipolar pace/shock lead. In another exemplary configuration, one or more additional electrodes, e.g., a ring electrode, may be included in the ventricular lead system 104. The additional ring electrode and the RV-tip electrode 112 may be used for bipolar sensing of cardiac signals. The atrial lead system 106 includes an A-tip electrode 152 and an A-ring electrode 154. In one embodiment, the atrial lead system 106 is configured as an atrial J lead.

In this configuration, the intracardiac lead system 102 is positioned within the heart 101, with portions of the atrial lead system 106 extending into the right atrium 120 and portions of the ventricular lead system 104 extending into the right atrium 120 and right ventricle 118. In particular, the A-tip electrode 152 and A-ring electrode 154 are positioned at appropriate locations within the right atrium 120. The RV-tip electrode 112 and RV-coil 114 electrodes are positioned at appropriate locations within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1 are defibrillation electrodes.

Additional pacing and defibrillation electrodes may also be included in the intracardiac lead system 102 to allow for various bipolar sensing, pacing, and defibrillation capabilities. For example, the intracardiac lead system 102 may include endocardial pacing and cardioversion/defibrillation leads (not shown) that are advanced into the coronary sinus and coronary veins to locate the distal electrode(s) adjacent to the left ventricle or the left atrium. Other intracardiac lead and electrode arrangements and configurations known in the art are also possible and considered to be within the scope of the present system.

The ventricular and atrial lead systems 104, 106 include conductors for communicating sense, pacing, and defibrillation/cardioverter signals between the cardiac defibrillator 100 and the electrodes and coils of the lead systems 104, 106. As is shown in FIG. 1, ventricular lead system 104 includes a conductor 108 for transmitting sense and pacing signals between the RV-tip electrode 112 and an RV-tip terminal 202 of the cardiac defibrillator 100. A conductor 110 of the ventricular lead system 104 transmits sense signals between the RV-coil or ring electrode 114 and an RV-coil terminal 204 of the cardiac defibrillator 100. The ventricular lead system 104 also includes conductor 122 for transmitting sense and defibrillation signals between terminal 206 of the cardiac defibrillator 100 and SVC-coil 116. The atrial lead system 106 includes conductors 132, 134 for transmitting sense and pacing signals between terminals 212, 210 of the cardiac defibrillator 100 and A-tip and A-ring electrodes 152 and 154, respectively.

Figure 2:
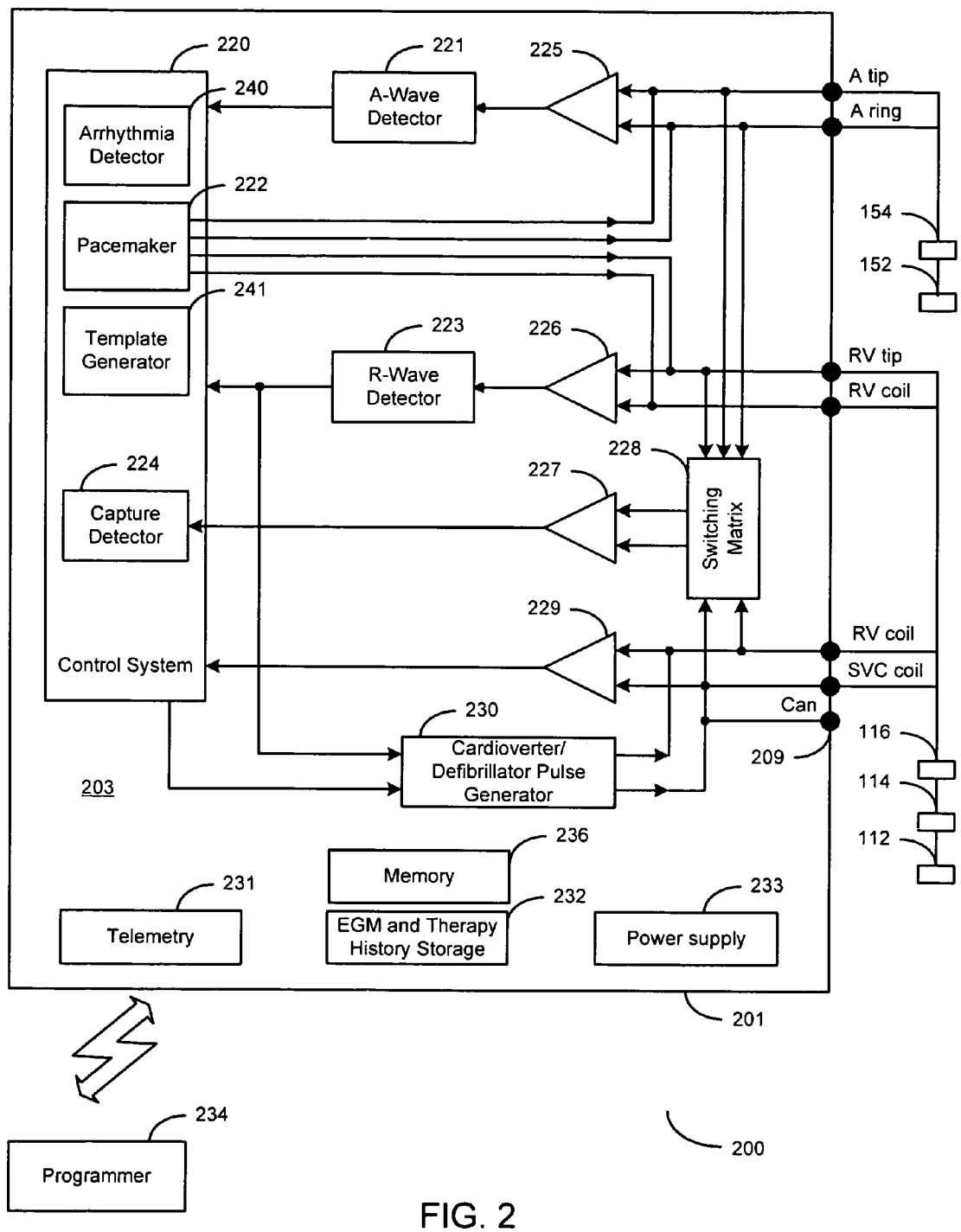
FIG. 2 is a block diagram of an implantable medical device with which capture verification and fusion/pseudofusion detection of the present invention may be implemented.

Referring now to FIG. 2, there is shown an embodiment of a cardiac defibrillator 200 suitable for implementing a capture verification methodology of the present invention. FIG. 2 shows a cardiac defibrillator divided into functional blocks. It is understood by those skilled in the art that there exist many possible configurations in which these functional blocks can be arranged. The example depicted in FIG. 2 is one possible functional arrangement. The cardiac defibrillator 200 includes circuitry for receiving cardiac signals from a heart (not shown in FIG. 2) and delivering electrical stimulation energy to the heart. The cardiac defibrillator 200 includes terminals for connecting the cardiac defibrillator 200 to the electrodes of the intracardiac lead system as previously discussed.

In one embodiment, the cardiac defibrillator circuitry 203 of the cardiac defibrillator 200 is encased and hermetically sealed in a housing 201 suitable for implanting in a human body as is known in the art. Power to the cardiac defibrillator 200 is supplied by an electrochemical battery 233 that is housed within the cardiac defibrillator 200. A connector block (not shown) is additionally attached to the housing 201 of the cardiac defibrillator 200 to allow for the physical and electrical attachment of the intracardiac lead system conductors to the cardiac defibrillator 200 and the encased cardiac defibrillator circuitry 203.

The cardiac defibrillator circuitry 203 of the cardiac defibrillator 200 may be a programmable microprocessor-based system, including a control system 220 and a memory circuit 236. The memory circuit 236 stores parameters for various pacing, defibrillation, and sensing modes, and stores data indicative of cardiac signals received by other components of the cardiac defibrillator circuitry 203. The control system 220 and memory circuit 236 cooperate with other components of the cardiac defibrillator circuitry 203 to perform operations involving the capture verification according to the principles of the present invention, in addition to other sensing, pacing and defibrillation functions. The control system 220 may encompass additional functional components including a pacemaker 222, an arrhythmia detector 240 and template generator 241 along with other functions for controlling the cardiac defibrillator circuitry 203. A memory 232 is also provided for storing historical EGM and therapy data. The historical data may be used for various purposes to control the operations of the cardiac defibrillator 200 and may also be transmitted to an external programmer unit 234 as needed or desired.

Telemetry circuitry 231 is additionally coupled to the cardiac defibrillator circuitry 203 to allow the cardiac defibrillator 200 to communicate with an external programmer unit 234. In one embodiment, the telemetry circuitry 231 and the programmer unit 234 use a wire loop antenna and a radio frequency telemetric link, as is known in the art, to receive and transmit signals and data between the programmer unit 234 and the telemetry circuitry 231. In this manner, programming commands may be transferred to the control system 220 of the cardiac defibrillator 200 from the programmer unit 234 during and after implant. In addition, stored cardiac data pertaining to capture verification and capture threshold, along with other data, may be transferred to the programmer unit 234 from the cardiac defibrillator 200, for example.

Cardiac signals sensed through use of the RV-tip electrode 112 are near-field signals or rate channel signals as are known in the art. More particularly, a rate channel signal is detected as a voltage developed between the RV-tip electrode 112 and the RV-coil 114. Cardiac signals sensed through use of one or both of the defibrillation coils or electrodes 114, 116 are far-field signals, also referred to as morphology or shock channel signals, as are known in the art. More particularly, a shock channel signal is detected as a voltage developed between the RV-coil 114 and the SVC-coil 116. A shock channel signal may also be detected as a voltage developed between the RV-coil 114 and the can electrode 209. Alternatively, the can electrode 209 and the SVC-coil electrode 116 may be shorted and a shock channel signal sensed as the voltage developed between the RV-coil 114 and the can electrode 209/SVC-coil 116 combination. Shock channel signals developed using appropriate combinations of the RV-coil, SVC-coil, and can electrodes 114, 116 and 209 are sensed and amplified by a shock EGM amplifier 229. The output of the EGM amplifier 229 is coupled to the control system 220.

In the embodiment of the cardiac defibrillator 200 depicted in FIG. 2, RV-tip and RV-coil electrodes 112, 114 are shown coupled to a V-sense amplifier 226 and thus to an R-wave detector 223. Rate channel signals received by the V-sense amplifier 226 are communicated to the R-wave detector 223, which serves to sense and amplify the rate channel signals, e.g. R-waves. The sensed R-waves may then be communicated to the control system 220.

A-tip and A-ring electrodes 152, 154 are shown coupled to an A-sense amplifier 225. Atrial sense signals received by the A-sense amplifier 225 are communicated to an A-wave detector 221, which serves to sense and amplify the A-wave signals. The atrial signals may be communicated from the A-wave detector 221 to the control system 220.

The pacemaker 222 communicates pacing signals to the RV-tip and A-tip electrodes 112 and 152 according to a preestablished pacing regimen under appropriate conditions. Blanking circuitry (not shown) is employed in a known manner when a ventricular or atrial pacing pulse is delivered, such that the ventricular channel, atrial channel, and shock channel are properly blanked at the appropriate time and for the appropriate duration.

A switching matrix 228, according to one may be coupled to the A ring 154, RV tip 112, RV coil 114 and SVC coil 116 electrodes. The switching matrix 228 can be arranged to provide connections to various configurations of pacing and defibrillation electrodes. The outputs of the switching matrix 228 are coupled to an evoked response (ER) amplifier 227 which serves to sense and amplify signals detected between the selected combinations of electrodes. The detected signals are coupled through the ER amplifier 227 to a capture detector 224. The capture detector 224 includes circuitry configured to detect an evoked response, detect fusion/pseudofusion, and verify capture in accordance with the invention.

The cardiac defibrillator 200 depicted in FIG. 2 is well-suited for implementing a capture detection methodology according to the principles of the present invention. In the embodiment illustrated in FIG. 2, the capture verification processes of the present invention are primarily carried out by the capture detector 224 in cooperation with the template generator 241 and other components of the control system 220.

The shock channel and rate channel signals used for template operations in connection with capture verification may be provided by the shock EGM amplifier 229 and the V-sense amplifier 226, respectively. It is understood that the required shock and rate channel signals may be developed and processed by components other than those depicted in FIG. 2 for system architectures that differ from the system architectures described herein.

A cardiac signal representing a captured beat may be described in terms of a pacing artifact superimposed on an evoked response. The evoked response represents the portion of the cardiac signal generated primarily by the contractile response of the heart to the pacing pulse. When a pace pulse does not produce a contractile response, capture does not occur, and an evoked response signal is not produced by the heart. The pacing artifact represents the portion of the cardiac signal arising from signal components other than the evoked response, and is typically significantly larger than the evoked response. The pacing artifact may be affected, for example, by lead polarization, after pace potential, lead impedance, patient impedance, pacer pulse width, and recharge timing.

The evoked response may be discerned by canceling the pacing artifact from a cardiac signal associated with a captured response. Methods for using the pacing artifact canceled signal to determine capture are described in commonly owned U.S. patent application entitled "Method and System for Detecting Capture with Cancellation of Pacing Artifact," concurrently filed on Dec. 31, 2002 and assigned Ser. No. 10/335,534, which is hereby incorporated herein by reference in its entirety.

Figure 3:
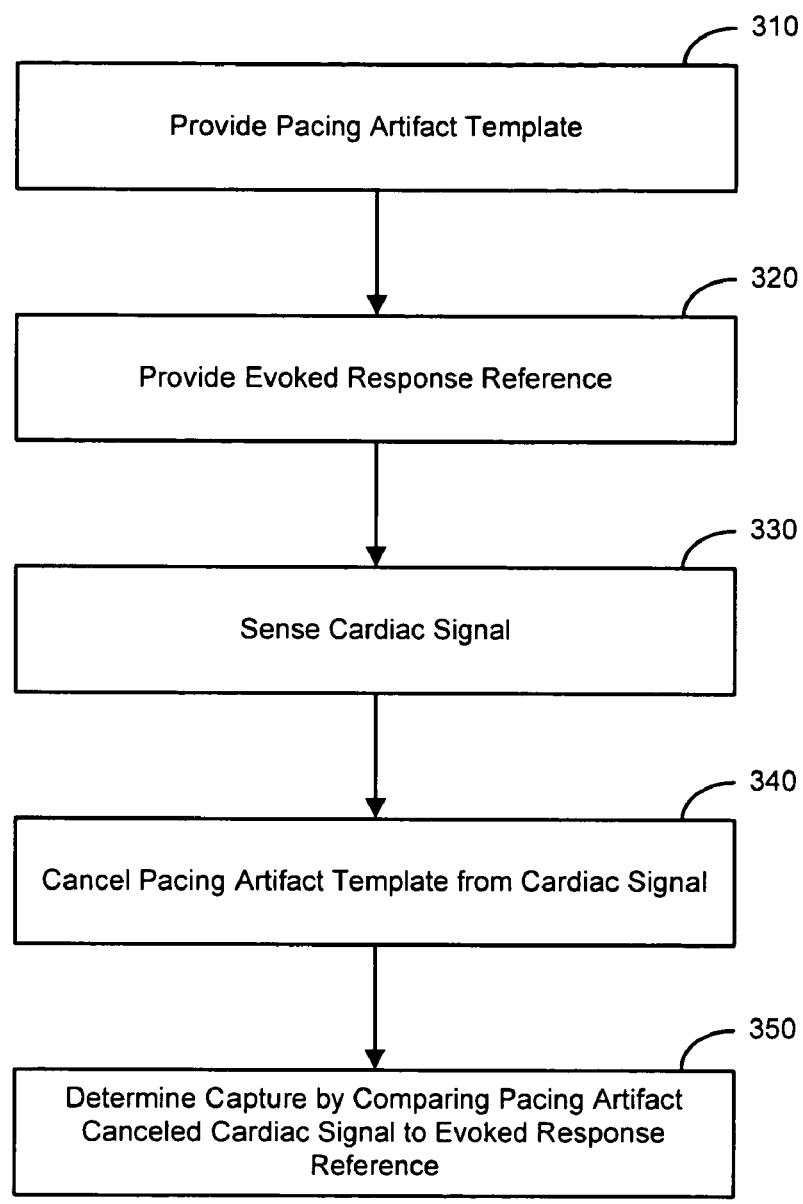
FIG. 3 is a flowchart of a method of detecting capture in accordance with an embodiment of the present invention.

According to the principles of the invention, capture verification includes using a pacing artifact captured cardiac signal and an evoked response reference. The evoked response reference is determined using the pacing artifact template. FIG. 3 is a flowchart illustrating various processes for capture verification according to the principles of the present invention. According to an example embodiment of the invention illustrated in the flowchart of FIG. 3, a pacing artifact template representative of the pacing artifact component of a cardiac signal is provided 310. An evoked response reference indicative of the evoked response component of a captured beat, is also provided 320. The evoked response reference is determined using the pacing artifact template. A cardiac signal is sensed 330 following a pace pulse. The pacing artifact template is canceled from the sensed cardiac signal 340. Capture is determined by comparing 350 the resultant pacing artifact canceled cardiac signal to the evoked response reference.

Figure 4:
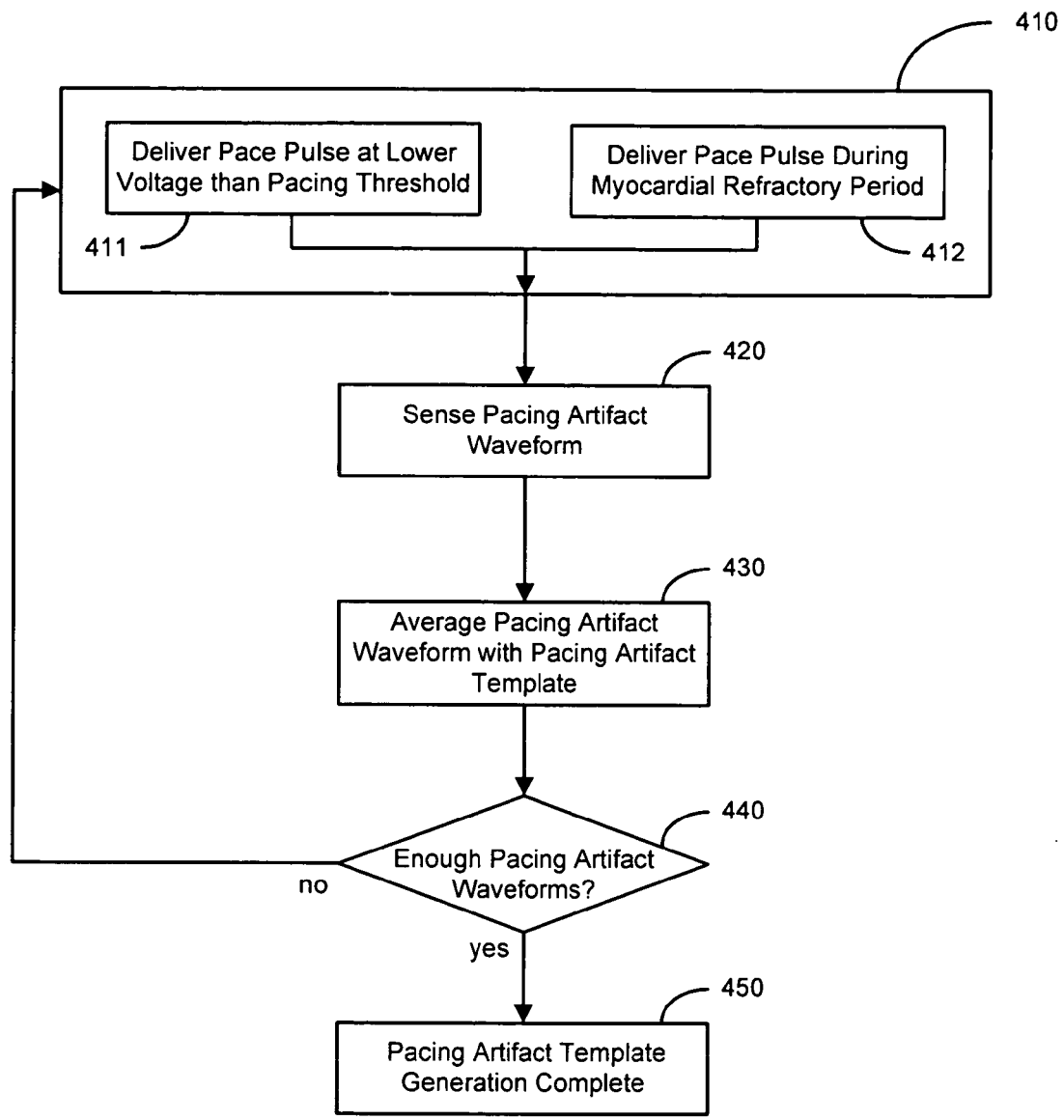
FIG. 4 is a flowchart of a method of forming a pacing artifact template in accordance with an embodiment of the present invention.

FIG. 4 illustrates a method of generating a pacing artifact template according to an embodiment of the present invention. In the embodiment illustrated by FIG. 4, an initial pacing artifact template may be formed by delivering a pulse at a low voltage or during a myocardial refractory period. Either method may be used to generate a pacing artifact waveform without a superimposed evoked response. The pacing artifact waveform may be sensed in a capture verification window and stored as an initial pacing artifact template. Additional pacing artifact waveforms may be combined with the initial pacing artifact template by averaging the pacing artifact waveform with the pacing artifact template, for example.

The additional pacing artifact waveforms used to update the initial template may be produced by pulses delivered 410 to the heart in such a way that capture does not occur. Thus, each pulse results in a pure pacing artifact waveform without a superimposed evoked response. Pure pacing artifact waveforms may be produced, for example, by pace pulses delivered 411 to the heart at an energy level lower than the capture threshold. In one embodiment, the additional pacing artifact waveforms delivered are pacing artifact waveforms generated by the last 10 pace pulses of a capture threshold stepdown test. Alternatively, the additional pacing artifact waveforms may be generated by pulses delivered 412 during a myocardial refractory period during a time the pulses cannot produce an evoked response.

Following generation of a pace pulse 410 by either of the methods discussed above, the pacing artifact waveform is sensed 420 in the cardiac verification window. The sensed pacing artifact waveforms may be combined with the pacing artifact template, for example, by averaging 430 the pacing artifact waveforms with the pacing artifact template sample by sample. When a predetermined number of pacing artifact waveforms have been collected 440, pacing artifact template generation is complete 450 and the pacing artifact template may be stored.

The pacing artifact may exhibit small variations in morphology with respect to pace pulse amplitude. Accordingly, the use of multiple pacing artifact templates corresponding to various pace pulse amplitudes may provide a more thorough cancellation of the pacing artifact over a range of pace pulse amplitudes, e.g., as used in a pacing threshold test. The method illustrated in FIG. 4 can be applied to generate pacing artifact templates for each pacing pulse amplitude of interest.

Alternatively, or additionally, a set of two or more pacing artifact templates may be generated, wherein a particular pacing artifact template characterizes the pacing artifact associated with a small range of pace pulse amplitudes. A pacing artifact template for a pace pulse range can be formed by combining pacing artifact waveforms from various pace pulse amplitudes within the range using, for example, an averaging operation. The pacing artifact template for a pace pulse range may also be formed by selecting a pacing artifact waveform at a single pace pulse amplitude, e.g., a pacing artifact waveform for a pulse amplitude near the center of the range to be characterized. The set of pacing artifact templates correspond to the entire pace pulse amplitude range to be evaluated.

The artifact waveform measurement may be accomplished during the refractory period of the myocardium. Pace pulses delivered during the refractory period produce pacing artifact waveforms without the evoked response components. The timing of the pace pulse delivered for pacing artifact measurement in the myocardial refractory period should be selected to be before the vulnerable period of the myocardium to avoid pro-arrhythmia, and after the deflections from the myocardial response from the previous cardiac event in the chamber have passed, e.g., 80 ms after the preceding cardiac event.

A pacing artifact may have a shape within the capture verification window that may be characterized by a function. The shape of the pacing artifact may be characterized by an exponentially decaying function in the capture verification window, for example. According to an example embodiment, a number of pacing artifact waveforms sensed during a capture verification window may be combined to form a pacing artifact template. A time constant of the pacing artifact template is determined and the pacing artifact template is predicted using the estimated time constant.

Although the examples provided herein predict the pacing artifact using an exponential function, those skilled in the art will recognize that prediction of the pacing artifact is not limited to characterization by an exponential function. Any function or combination of functions may be used to characterize and predict the pacing artifact.

Figure 5:
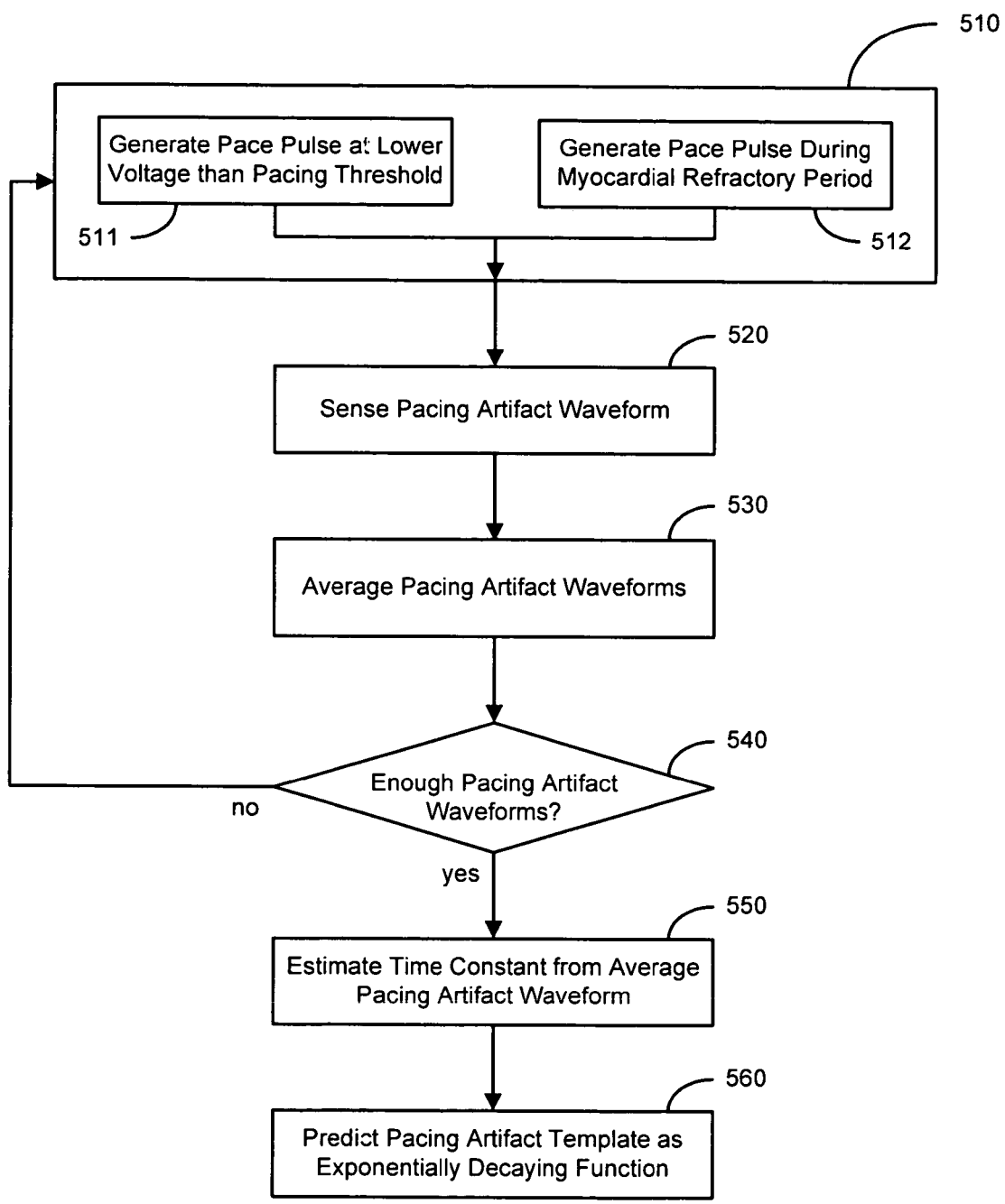
FIG. 5 is a flowchart of a method of predicting a pacing artifact template as an exponentially decaying function in accordance with an embodiment of the present invention.

In the exemplary embodiment illustrated by FIG. 5, a pacing artifact template is determined by delivering 510 a predetermined number of pulses to the heart and sensing 520 the resultant pacing artifact waveforms in a capture verification window. The pulses are delivered 510 in such a way that capture does not occur, resulting in the production of pure pacing artifact waveforms without a superimposed evoked response. The pulses may be delivered at an energy level below the capture threshold 511, for example. Alternatively, the pace pulses may be delivered during a myocardial refractory period at a time when pulses delivered to the heart do not produce an evoked response 512.

Following delivery 510 of a pulse by either method, the resultant pacing artifact waveform is sensed 520 in the capture verification window. The sensed pacing artifact waveform is combined 530 with the previously acquired waveforms. For example, the pacing artifact waveform may be averaged with previously acquired pacing artifact waveforms, if any.

The process of delivering a pulse and detecting the resultant pacing artifact waveform 510–530 may be repeated until a predetermined number of pacing artifact waveforms have been acquired 540. After the predetermined number of pacing artifact waveforms have been acquired 540, a time constant of the average pacing artifact waveform is estimated 550. The pacing artifact template is predicted as an exponentially decaying function 560 in the capture verification window using the estimated time constant.

A pacing artifact template generated by either of the methods described in the preceding paragraphs with reference to FIGS. 4 and 5 may be periodically updated as required or desired. For example, a pacing artifact template may be updated by averaging additional pacing artifact waveforms with the existing pacing artifact template.

Figure 6:
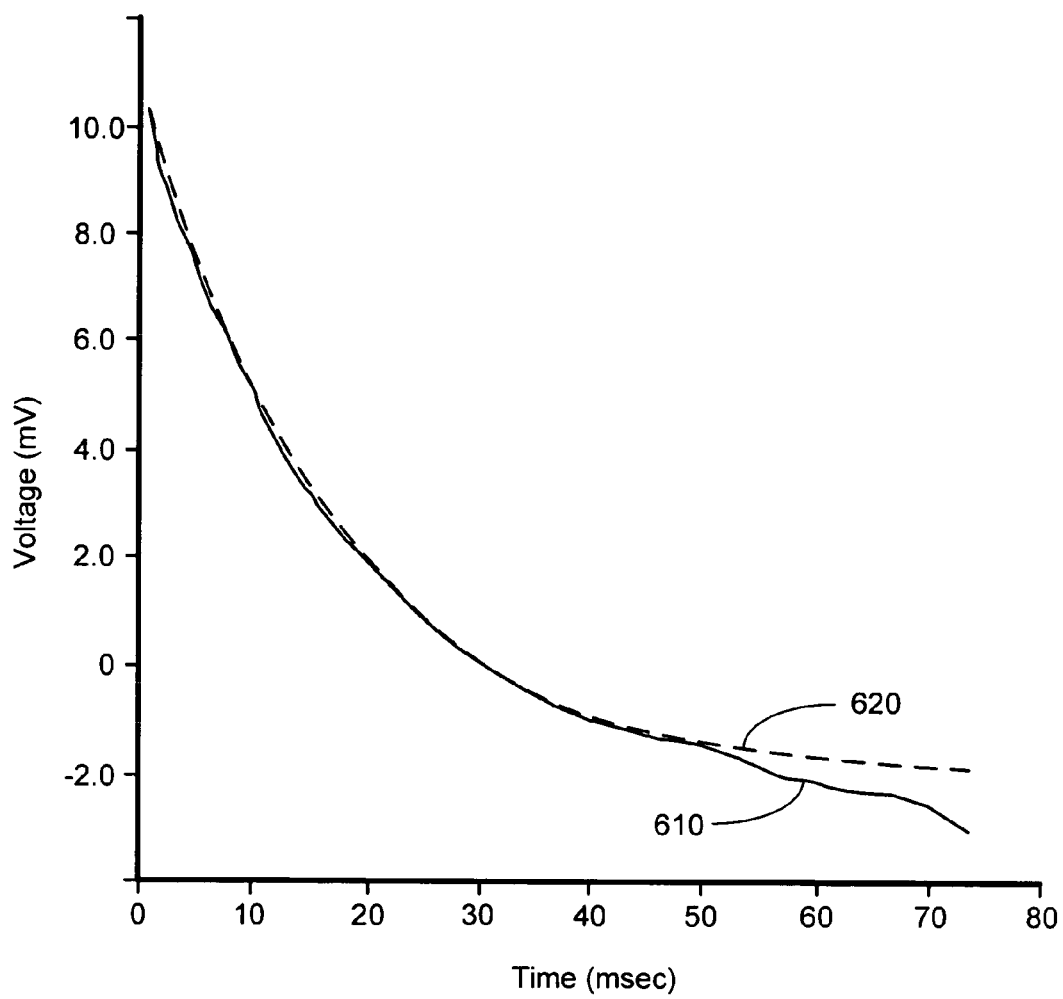
FIG. 6 is a graph comparing a predicted pacing artifact to a pacing artifact template.

FIG. 6 shows a comparison of a graph of a pacing artifact template 610 representing the average of a number of pacing artifact waveforms and a graph of the pacing artifact template predicted as an exponentially decaying function 620. The pacing artifact template can be predicted for a sampled signal using Equation (1):

$$x(t)=A*x(t-1) \qquad (1)$$

where $A=e^{-T/a}$ where x(t) represents a current sample of the pacing artifact template, x(t−1) represents a previous sample of the pacing artifact template, and A is a constant derived from the estimated time constant of the pacing artifact template, a, and the sample time, T.

According to an embodiment of the invention, a signal corresponding to the pacing artifact template may be generated by hardware using digital circuitry to produce a signal corresponding to the function of Equation (1). The normalized pacing artifact template signal generated in hardware may be used to cancel the pacing artifact from a sensed cardiac signal in the capture verification window. In other embodiments, the normalized pacing artifact template may be canceled from the sensed cardiac signal using software-based techniques. For example, the pacing artifact template may be canceled by subtracting stored or predicted values of the pacing artifact template from the sensed cardiac signal at each sample point in the capture verification window.

In accordance with various embodiments of the invention, a cardiac signal representing an evoked response may be characterized by an evoked response reference. The evoked response reference characterizes only the evoked response component of a captured response, without a superimposed pacing artifact. The evoked response reference may be used to detect capture.

A cardiac signal following a pace pulse is sensed and the pacing artifact template is canceled from the cardiac signal. This procedure removes the pacing artifact from the cardiac signal, leaving only the evoked response portion of the cardiac signal, if capture occurred. The pacing artifact canceled cardiac signal is compared to an evoked response reference. The evoked response reference may be, for example, an evoked response template, an amplitude reference, or other indicators associated with an evoked response. Capture verification is implemented by comparing the evoked response reference to the pacing artifact canceled cardiac signal following a pace pulse. If a sufficient number of paced cardiac responses are comparable to the evoked response reference, then capture may be established.

Figure 7:
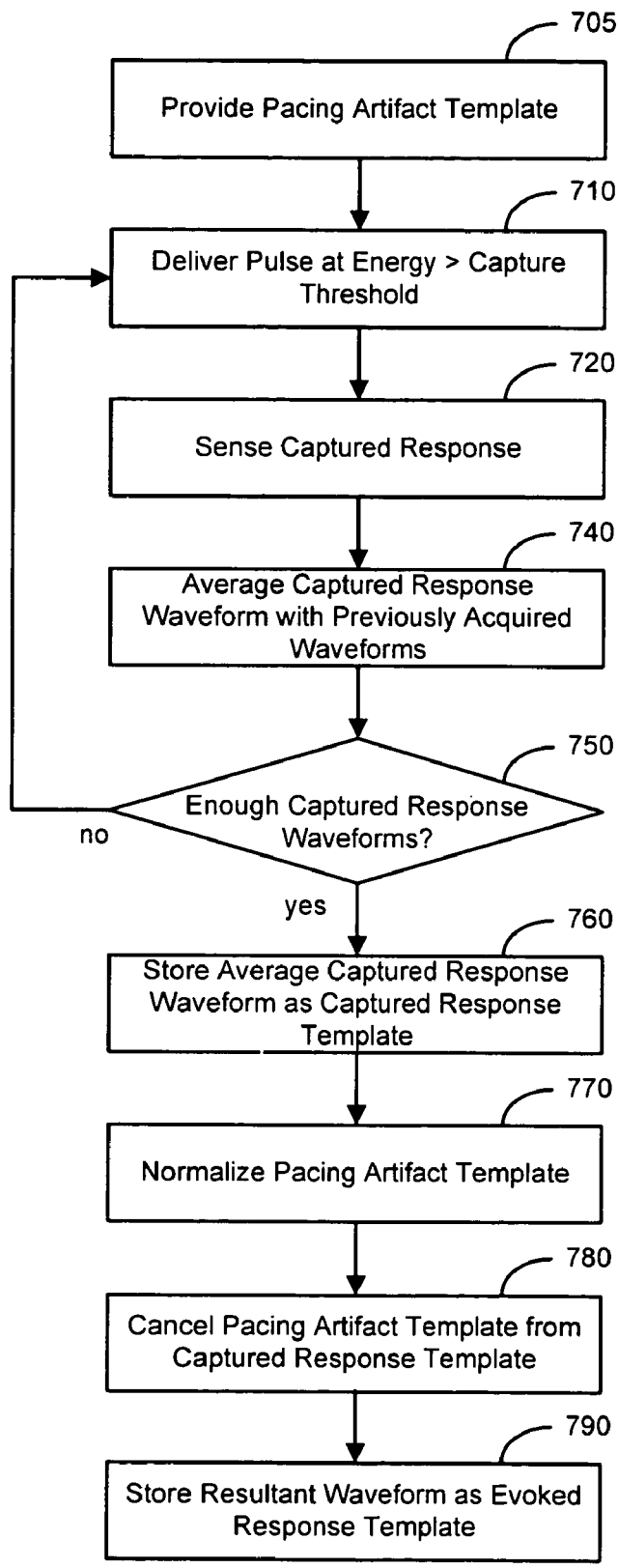
FIG. 7 is a flowchart of a method of forming an evoked response template in accordance with an embodiment of the present invention.

FIG. 7 illustrates a method of providing an evoked response template for use in capture verification in accordance with an embodiment of the invention. The heart is stimulated by pace pulses having a voltage greater than the capture threshold. The resultant captured cardiac responses are sensed and averaged. A pacing artifact template is subtracted or otherwise cancelled from the average captured response to produce an evoked response template.

Turning to a flowchart of this method illustrated in FIG. 7, a pacing artifact template is provided at block 705. For example, the pacing artifact template may be provided by either of the methods discussed in connection with FIG. 4 or 5. An average captured response may be determined by delivering a predetermined number of pace pulses at a pacing voltage greater than the capture threshold 710. Delivery of a pace pulse above the capture threshold produces a cardiac contraction. The captured response waveform resulting from the cardiac contraction is sensed 720 in the capture verification window. The sensed captured response waveform may be combined 740, for example, by averaging, with the previously acquired captured response waveforms.

Additional captured response signals may be generated 710 until a predetermined number of captured response waveforms have been acquired 750. The average captured response may be stored 760 as a captured response template.

The pacing artifact template is normalized 770 with respect to the captured response template in the capture verification window. Following normalization, the pacing artifact template is canceled from the captured response template 780. For example, the pacing artifact template may be canceled by subtracting the pacing artifact template from the captured response template sample by sample. Subtraction of the pacing artifact template from a captured response template results in an evoked response template 790, which may be stored for use in subsequent capture verification procedures. The evoked response template may be compared to pacing artifact cancelled cardiac signals to verify capture.

In another embodiment, the pacing artifact template may be normalized and canceled from a number of captured response beats. The pacing artifact template canceled beats may then be averaged to produce the evoked response template.

Figure 8B:
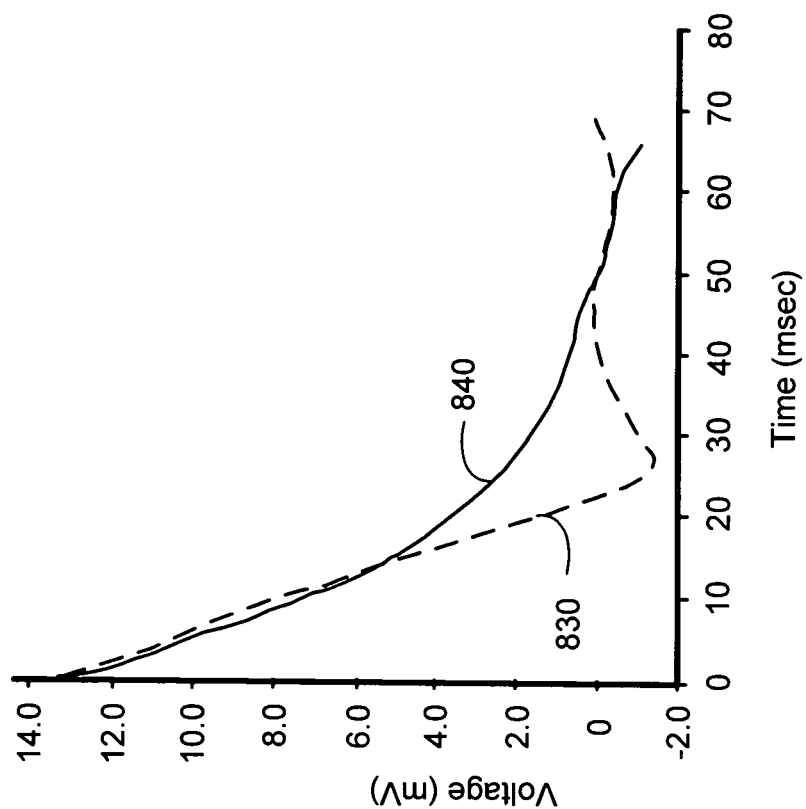
FIGS. 8A and 8B are graphs illustrating normalization of a pacing artifact template in accordance with an embodiment of the invention.
Figure 8A:
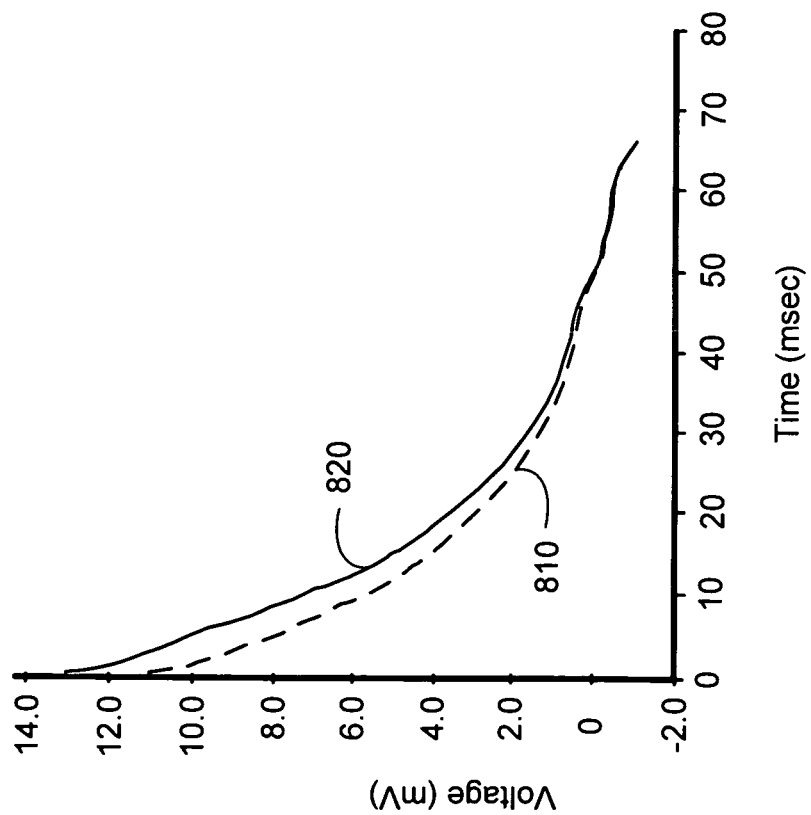

Normalization of the pacing artifact template with respect to a cardiac signal is illustrated in FIGS. 8A and 8B. FIG. 8A shows a graph of a pacing artifact template before normalization 810 and after normalization 820 using one or more values of a sensed cardiac signal 830 in the capture verification window. FIG. 8B shows the graph of a normalized pacing artifact template 840 overlaying the graph of a sensed cardiac signal 830 that includes an evoked response.

Figure 9:
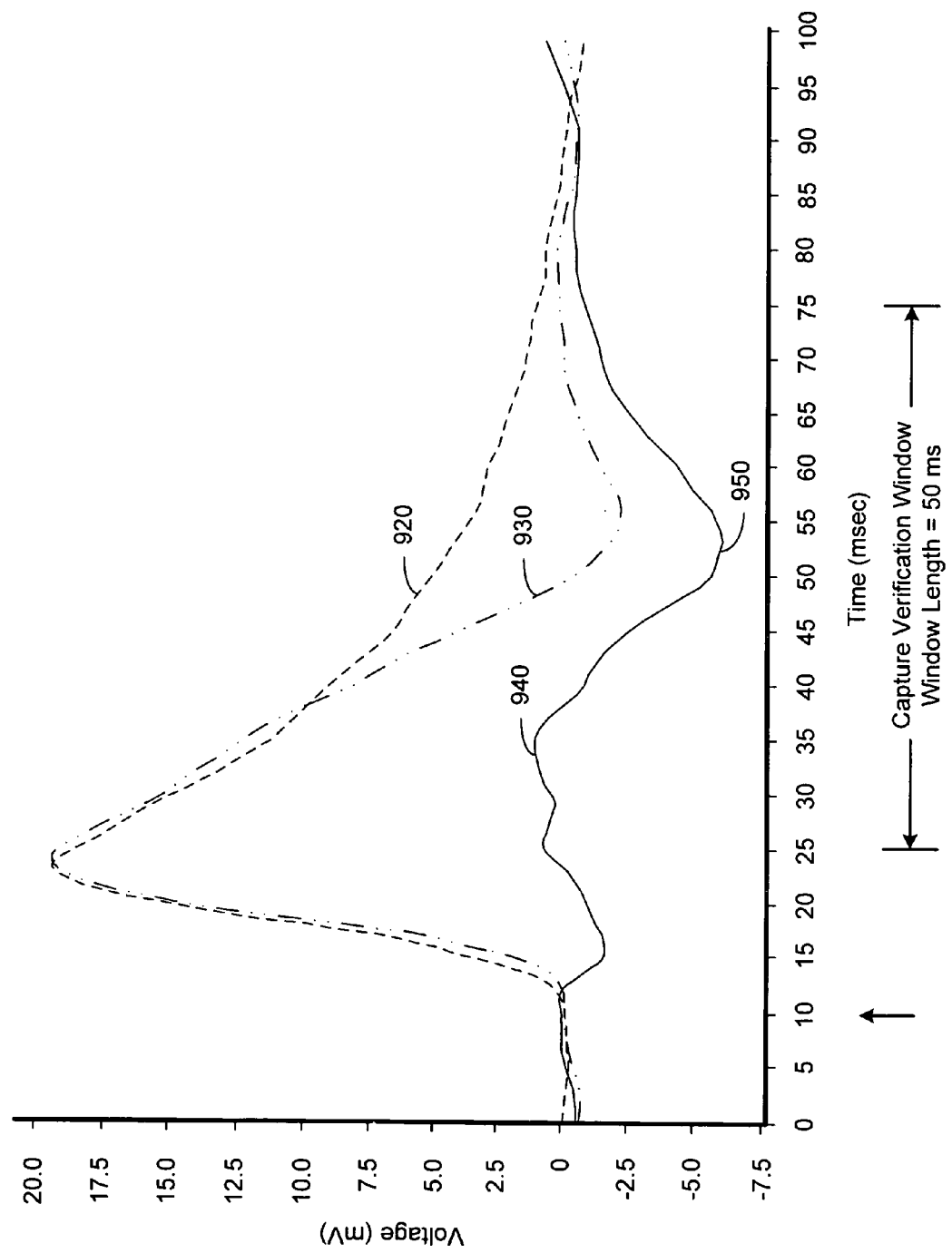
FIG. 9 is a graph illustrating cancellation of a pacing artifact template from a sensed cardiac signal in accordance with an embodiment of the invention.

Cancellation of a pacing artifact template from a sensed cardiac signal in accordance with the invention is illustrated in FIG. 9. A capture verification window commences approximately 25 ms following delivery of the pacing pulse and extends for approximately 50 ms. The pacing artifact template 920 is shown overlaying the sensed cardiac waveform of a captured beat 930. Cancellation of the pacing artifact template 920 from the sensed cardiac waveform 930 results in a pacing artifact canceled waveform 940 from which capture is determined. In the example of FIG. 9, capture is indicated by the presence of the local minima 950 at approximately 53 ms following the pace pulse.

Capture may be verified by comparing the pacing artifact canceled cardiac signal with the evoked response template.

In one implementation, the comparison may be accomplished by calculating a correlation coefficient (CC) of pacing artifact canceled cardiac signal and the evoked response template by a technique such as Correlation Waveform Analysis (CWA). Using this technique, correlation coefficient (CC) may be calculated to compare the pacing artifact canceled cardiac signal to the evoked response template. In one particular embodiment, Equation 2, provided below, is used to compute the CC between the samples of a pacing artifact cancelled cardiac beat and the evoked response template samples.

$$CC = \frac{N\sum_{i=1}^{N} X_i Y_i - \left(\sum_{i=1}^{N} X_i\right)\left(\sum_{i=1}^{N} Y_i\right)}{\sqrt{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)}} \quad [2]$$

where, Xi represents template N samples and Yi represents beat N samples in this illustrative example. Typically, the number of samples associated with each waveform or template is about 33 samples.

If the correlation coefficient is greater than a predetermined value, for example, about 0.71, the pacing artifact canceled cardiac signal is considered to represent an evoked response signal. Capture may be established when a predetermined number of cardiac responses following pace pulses of a particular energy level are correlated to the evoked response template. In one implementation, capture is established when three or more or the last four paced responses are correlated to the template.

The evoked response waveform may change gradually with time. This situation may lead to erroneous capture verification because the evoked response template no longer represents an evoked response. Updating the evoked response template with evoked response waveforms correlated to the evoked response template mitigates this problem. The evoked response template may be updated using evoked response waveforms correlated to the evoked response template.

Figure 10:
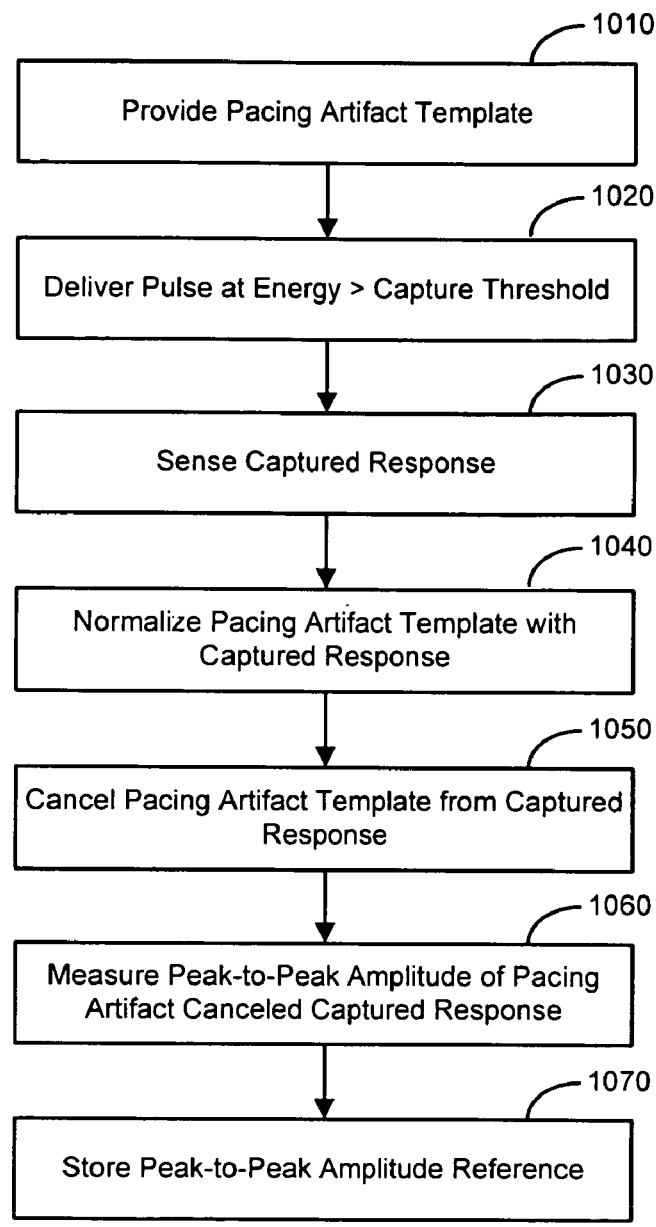
FIG. 10 is a flowchart of a method of providing a peak-to-peak amplitude reference in accordance with an embodiment of the present invention.

In another embodiment of the invention, a peak-to-peak amplitude indicative of an evoked response may be used as an evoked response reference. FIG. 10 illustrates the method of providing a peak-to-peak evoked response amplitude reference. A pacing artifact template is provided 1010, by either of the methods previously discussed in connection with FIG. 4 and FIG. 5. A pace pulse at a pacing voltage significantly above the pacing threshold, for example 4 volts, is delivered 1020 to the heart and the resulting cardiac signal is sensed 1030. The pacing artifact template is normalized with respect to the sensed cardiac signal 1040 in the cardiac verification window. Canceling the pacing artifact template from the sensed cardiac signal 1050 results in a signal associated with an evoked response. The peak-to-peak amplitude of the evoked response is measured 1060 and stored as the initial peak-to-peak amplitude reference 1070. The initial peak-to-peak amplitude reference may be subsequently updated by acquiring additional evoked responses and combining the peak-to-peak amplitudes of the additional evoked responses with the initial peak-to-peak amplitude reference.

According to methods of the invention, capture may be detected by comparing an evoked response reference to a pacing artifact canceled cardiac signal. The evoked response reference may be, for example, an evoked response template, a peak-to-peak amplitude reference, or any other reference or indicator associated with a captured cardiac response. The evoked response reference is representative of the cardiac signal of a captured beat.

Figure 11A:
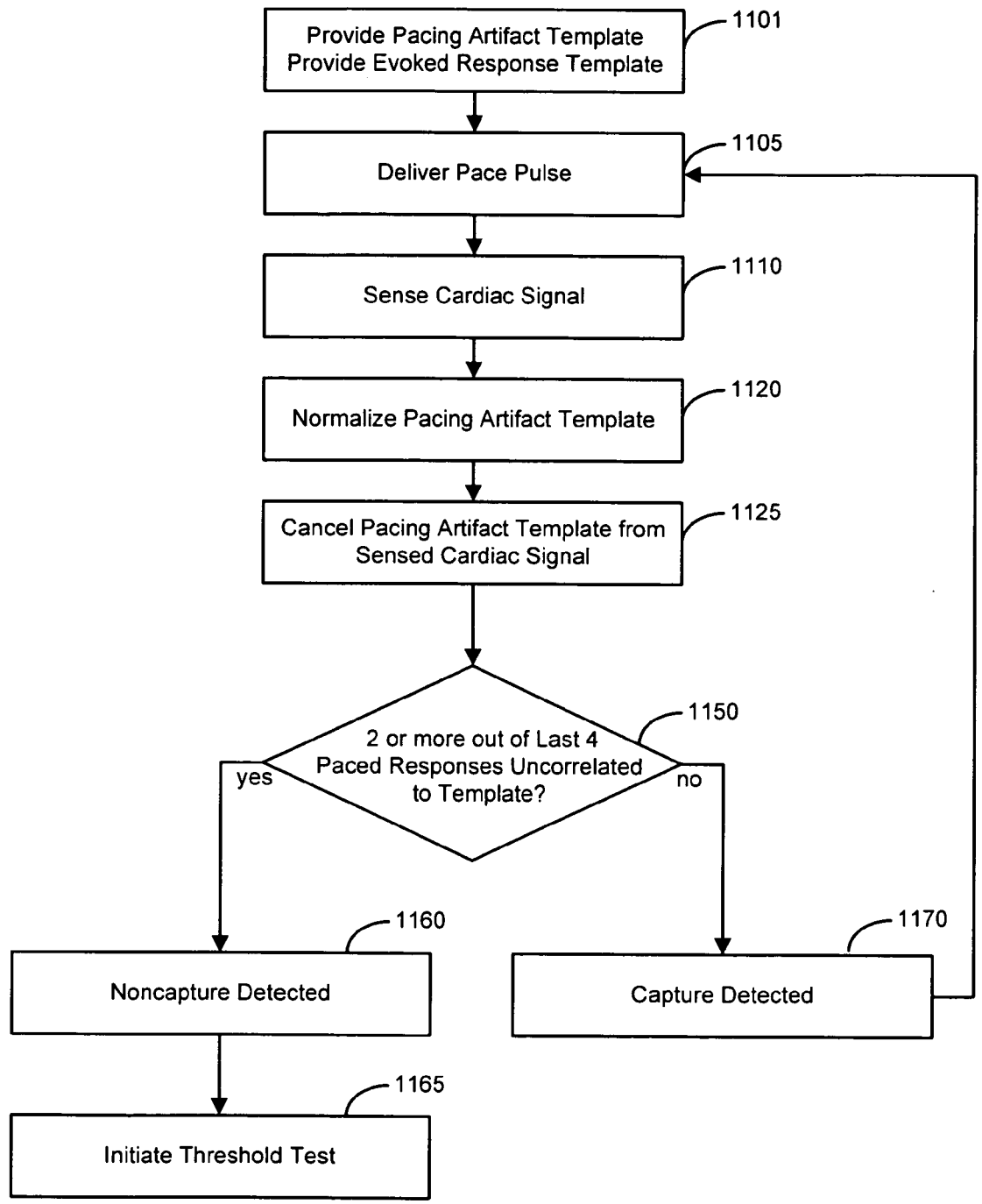
FIGS. 11A and 11B are flowcharts illustrating methods of detecting capture using an evoked response template in accordance with an embodiment of the present invention.

FIG. 11A illustrates a method of capture detection using an evoked response template for automatic capture verification in accordance with an embodiment of the invention. According to this exemplary embodiment, a pacing artifact template and an evoked response template are provided 1101 by methods previously discussed. A pace pulse is delivered 1105 and the cardiac signal following the pace pulse is sensed 1110. The pacing artifact template is normalized 1120 using one or more samples of the cardiac signal within the capture verification window. In one example, one or more samples of the cardiac signal are averaged and the pacing artifact template normalized with respect to the average value. In another example, a representative set of the cardiac signal samples may be used to define a slope of the cardiac signal within the cardiac verification window. The pacing artifact template may be normalized with respect to a point extrapolated using the slope.

The pacing artifact template is canceled from the sensed cardiac signal 1125, for example, by subtracting the pacing artifact template from the cardiac signal sample by sample, to produce a pacing artifact canceled cardiac signal. If the pacing artifact canceled cardiac signal is correlated to the evoked response template, the pacing artifact canceled cardiac signal is detected as an evoked response When a predetermined number of consecutive beats have pacing artifact canceled cardiac signals uncorrelated to the evoked response template 1150, for example 2 or more beats out of the last 4 paced beats, non-capture is detected 1160. When noncapture is detected 1160, an automatic threshold test may be initiated 1165 to determine an appropriate pacing voltage. If capture is detected 1170, the process continues with the next paced beat 1105. A captured beat may be used to update the evoked response reference using, for example, a method described below in connection with FIG. 11B.

Figure 11B:
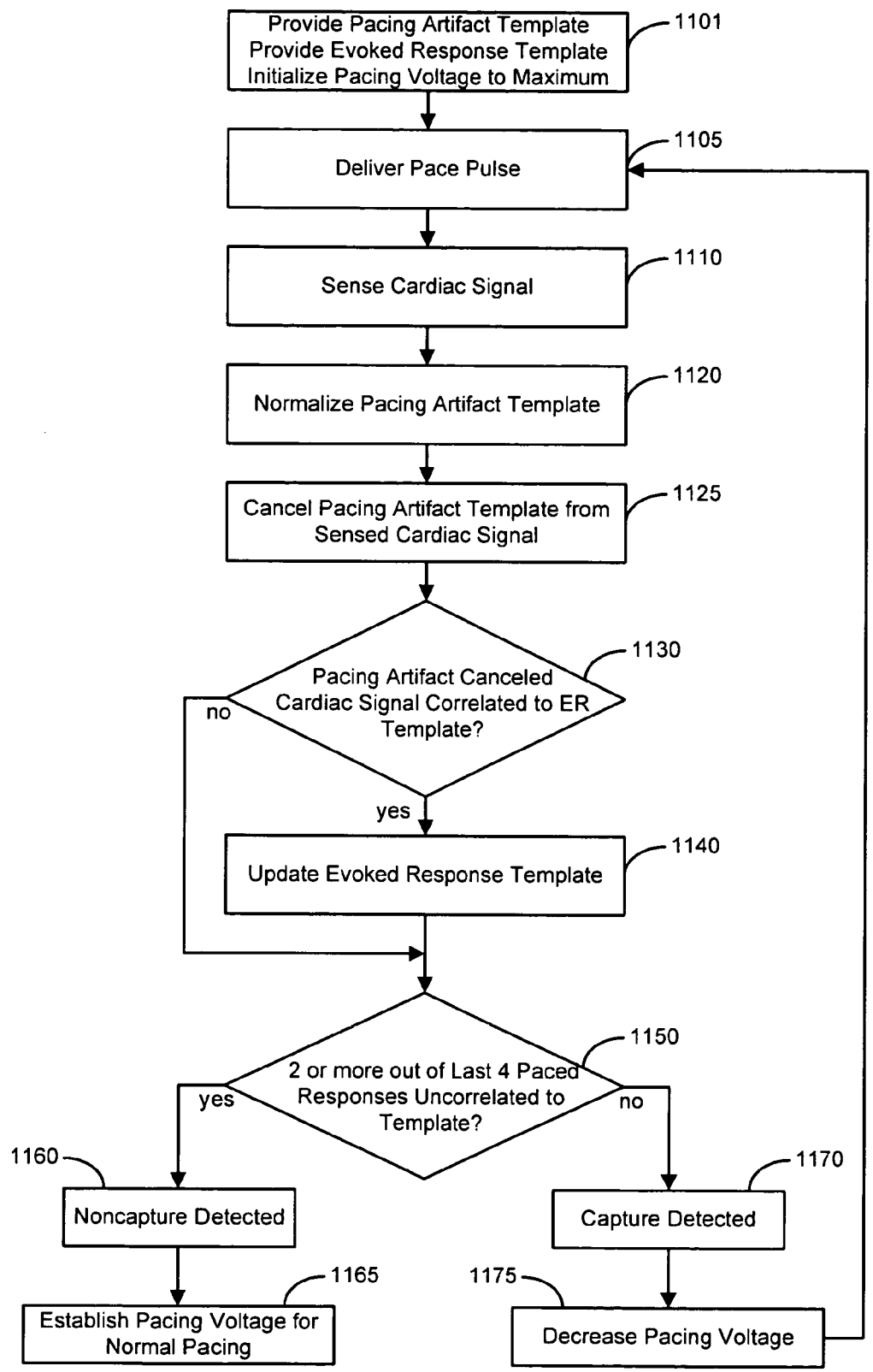

FIG. 11B illustrates a method of capture detection using an evoked response template for an automatic threshold process in accordance with an embodiment of the invention. According to this exemplary embodiment, a pacing artifact template and an evoked response template are provided by methods previously discussed.

A pace pulse is delivered 1105 and the cardiac signal following the pace pulse is sensed 1110. The pacing artifact template is normalized 1120 using one or more samples of the cardiac signal within the capture verification window. The pacing artifact template may be canceled 1125 from the sensed cardiac signal, for example, by subtracting the pacing artifact template from the cardiac signal sample by sample, to produce a pacing artifact canceled cardiac signal.

If the pacing artifact canceled cardiac signal is correlated 1130 to the evoked response template, the pacing artifact canceled cardiac signal is detected as an evoked response and may be used to update 1140 the evoked response template. In one example embodiment, a pacing artifact canceled cardiac signal is correlated to the evoked response template when CC is greater than a predetermined number, for example, 0.71.

If the pacing artifact canceled cardiac signal is correlated to the evoked response template 1130, the evoked response template may be updated 1140 with the pacing artifact canceled cardiac signal. The evoked response template may be updated using various techniques, e.g., using a weighted and/or moving average, or other processes. In one embodiment, Equation 3, provided below, is used to update each sample of the evoked response template with a temporally corresponding sample of the pacing artifact canceled cardiac signal in the cardiac verification window:

$$U_n = B_1 C_n + B_2 S_n \quad (3)$$

where $U_n$ represents the $n^{th}$ sample of the updated template, $C_n$ represents the $n^{th}$ sample of the current template, $S_n$ represents the $n^{th}$ sample of the pacing artifact canceled cardiac signal correlated to the evoked response template, and $B_1$ and $B_2$ are appropriate coefficients. In one example, $B_1$ and $B_2$ are set equal to 0.75 and 0.25, respectively. When a predetermined number of consecutive beats have pacing artifact canceled cardiac signals uncorrelated to the evoked response template 1150, for example 2 or more beats out of the last 4 paced beats, non-capture is detected 1160. An appropriate pacing voltage is established using a suitable safety margin 1165. If capture is detected 1170, the pacing voltage for the threshold test is decreased 1175 and the threshold determination process of blocks 1105–1150 continues until noncapture is detected.

Figure 12A:
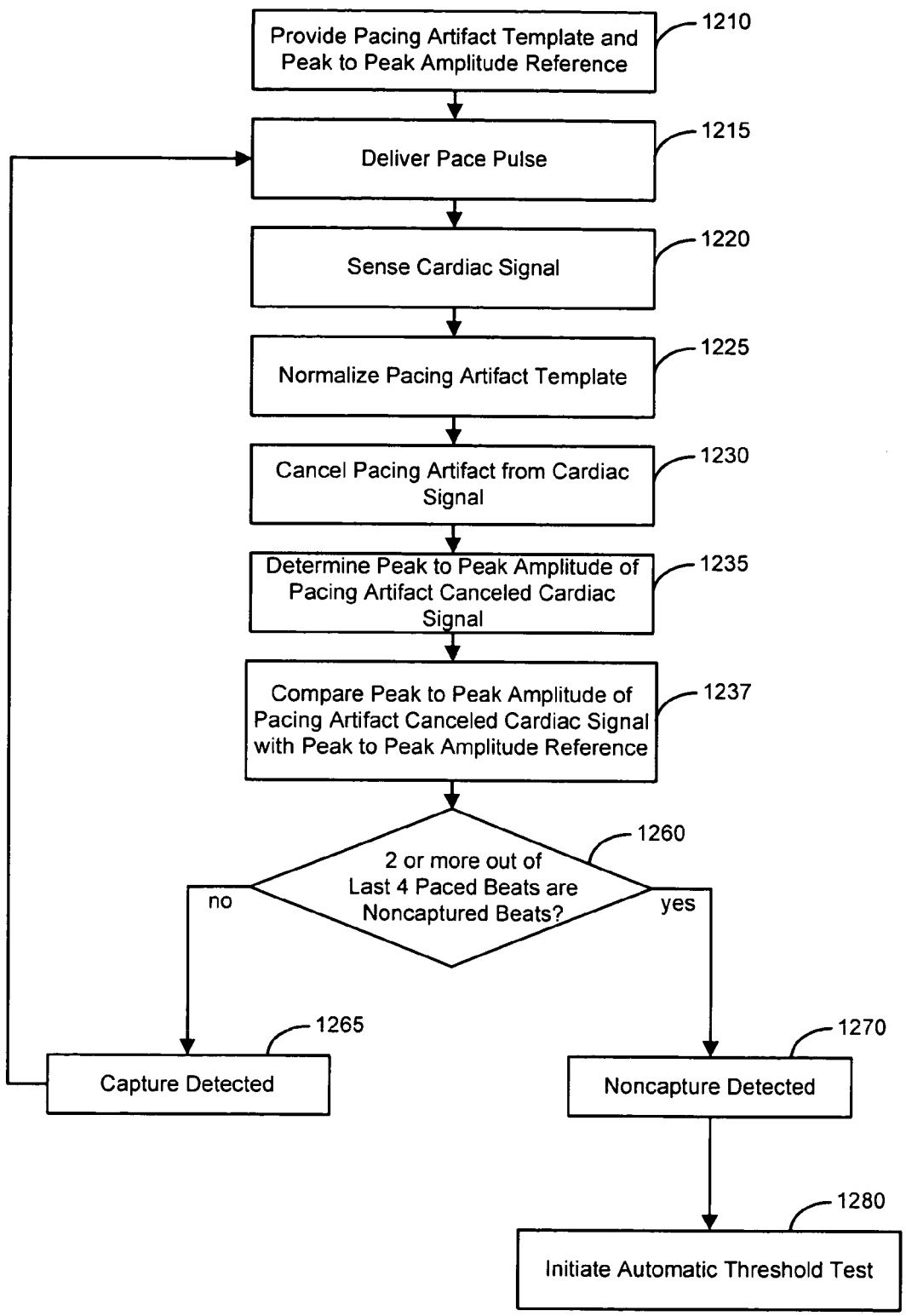
FIGS. 12A and 12B are flowcharts illustrating methods of detecting capture using a peak-to-peak amplitude reference in accordance with an embodiment of the present invention.

FIG. 12A illustrates a method of detecting capture using a peak-to-peak amplitude reference during an automatic capture verification process in accordance with an embodiment of the invention. A pacing artifact template and a peak-to-peak amplitude reference are provided 1210. The pacing artifact template may be provided, for example, by either of the methods discussed in connection with FIGS. 4 and 5. An initial peak-to-peak amplitude reference may be provided by the method discussed in connection with FIG. 10. A pace pulse is delivered 1215 and a cardiac signal following the pace pulse is sensed 1220. The pacing artifact template is normalized within the capture verification window with respect to the sensed cardiac signal 1225 and canceled from the sensed cardiac signal 1230 to derive the pacing artifact canceled cardiac signal. The peak-to-peak amplitude of the pacing artifact canceled cardiac signal is measured 1235 and compared to the peak-to-peak amplitude reference 1237. If the peak-to-peak amplitude of the pacing artifact canceled cardiac signal is less than or equal to a predetermined percentage of the peak-to-peak amplitude reference, for example, 50%, the cardiac signal is classified as a noncaptured beat. Otherwise, the cardiac signal is classified as a captured beat. The peak-to-peak amplitude of the captured beat may be used to update the peak-to-peak amplitude reference using, for example, a method described below in connection with FIG. 12B.

Noncapture may be detected 1270, for example, when a first predetermined number out of a second predetermined number of cardiac signals have peak-to-peak amplitudes less than or equal to a predetermined percentage of the peak-to-peak amplitude reference 1260. Otherwise, capture is detected 1265. For example, noncapture may be detected 1270 when 2 or more out of the last 4 paced beats have pacing artifact canceled cardiac signals with peak-to-peak amplitudes less than or equal to 50% of the peak-to-peak amplitude reference.

If capture is detected 1265, normal pacing continues and another cardiac signal is sensed 1220. However, if noncapture is detected 1270, an automatic threshold test may be initiated 1280 to determine an appropriate pacing energy level.

Figure 12B:
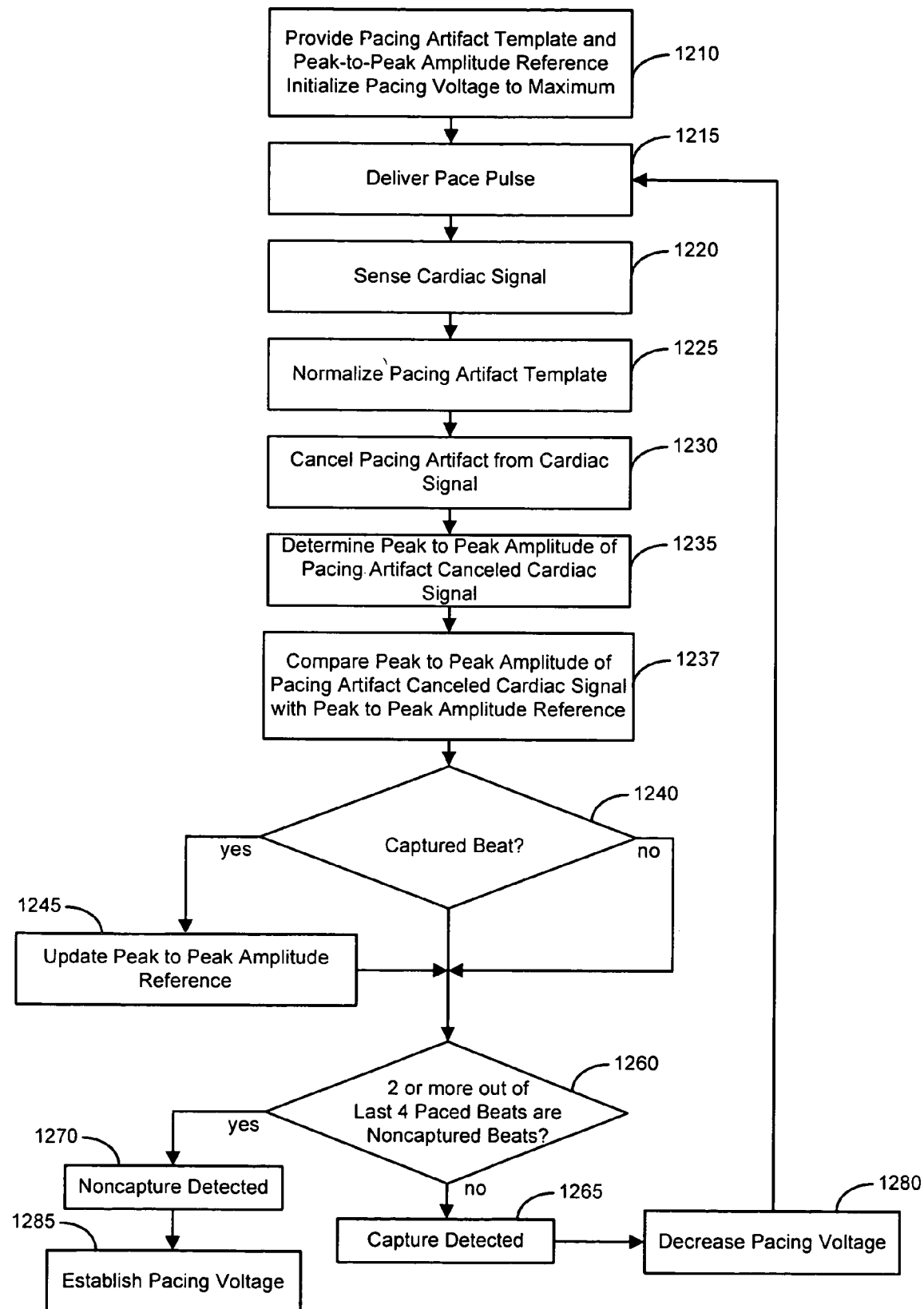

FIG. 12B illustrates a method of detecting capture using a peak-to-peak amplitude reference during a capture threshold test in accordance with an embodiment of the invention. A pacing artifact template and a peak-to-peak amplitude reference are provided, and the initial pacing voltage is set to a maximum value 1210. The pacing artifact template may be provided, for example, by either of the methods discussed in connection with FIGS. 4 and 5. An initial peak-to-peak amplitude reference may be provided by the method discussed in connection with FIG. 10.

A pace pulse is delivered 1215 and a cardiac signal following the pace pulse is sensed 1220. The pacing artifact template is normalized within the capture verification window with respect to the sensed cardiac signal 1225 and canceled from the sensed cardiac signal 1230 to derive the pacing artifact canceled cardiac signal. The peak-to-peak amplitude of the pacing artifact canceled cardiac signal is measured 1235 and compared to the peak-to-peak amplitude reference 1237. If the peak-to-peak amplitude of the pacing artifact canceled cardiac signal is less than or equal to a predetermined percentage of the peak-to-peak amplitude reference, for example, 50%, the cardiac signal is classified as a noncaptured beat. Otherwise, the beat is classified as a captured beat.

If a captured beat is detected 1240, the peak-to-peak amplitude of the pacing artifact canceled cardiac signal may be used to update the peak-to-peak amplitude reference 1245. The peak-to-peak amplitude reference may be updated using various techniques, e.g., using a weighted and/or moving average, or other processes. In one embodiment, the peak-to-peak amplitude of the pacing artifact canceled cardiac signal is used to update the peak-to-peak amplitude reference according to Equation 4 below:

$$U = B_1 C + B_2 S \quad (4)$$

where U represents the updated peak-to-peak amplitude reference, C represents the current peak-to-peak amplitude reference, S represents the peak-to-peak amplitude of the pacing artifact canceled cardiac signal, and $B_1$ and $B_2$ are appropriate coefficients. In one example, $B_1$ and $B_2$ are set equal to 0.75 and 0.25, respectively.

It may be appropriate to provide an upper and lower bound to the peak-to-peak amplitude reference as described in Equation 4 above. For example, for a ventricular chamber, the updated peak-to-peak amplitude reference may be constrained by an upper bound of 20 mV and a lower bound of 1 mV. Similarly, for an atrial chamber, the updated peak-to-peak amplitude reference may be constrained by an upper bound of 4 mV and a lower bound of 0.2 mV.

Noncapture may be detected, for example, when a predetermined number of cardiac signals have peak-to-peak amplitudes less than or equal to a predetermined percentage of the peak-to-peak amplitude reference 1260. Otherwise, capture is detected 1265. For example, noncapture may be detected 1270 when 2 or more out of the last 4 paced beats have pacing artifact canceled cardiac signals with peak-to-peak amplitudes less than or equal to 50% of the peak-to-peak amplitude reference. When noncapture is detected, the normal pacing voltage is established 1285 using a suitable safety margin. If capture is detected 1265, the pacing voltage is decreased by an incremental value and the threshold test continues until noncapture is detected.

As previously discussed, a situation known as fusion or pseudofusion may occur during pacing. A fusion beat occurs when an intrinsic cardiac depolarization of a particular chamber merges with a pacer output pulse within that chamber. Pseudofusion occurs when a pacer output pulse artifact is superimposed upon a spontaneous P wave during atrial pacing, or upon a spontaneous QRS complex during ventricular pacing. In pseudofusion, the pacing stimulus is ineffective because the tissue around the electrode has already spontaneously depolarized and is in its refractory period. During a capture verification procedure, it is desirable to detect fusion and pseudofusion beats to prevent false capture detection.

Figure 13A:
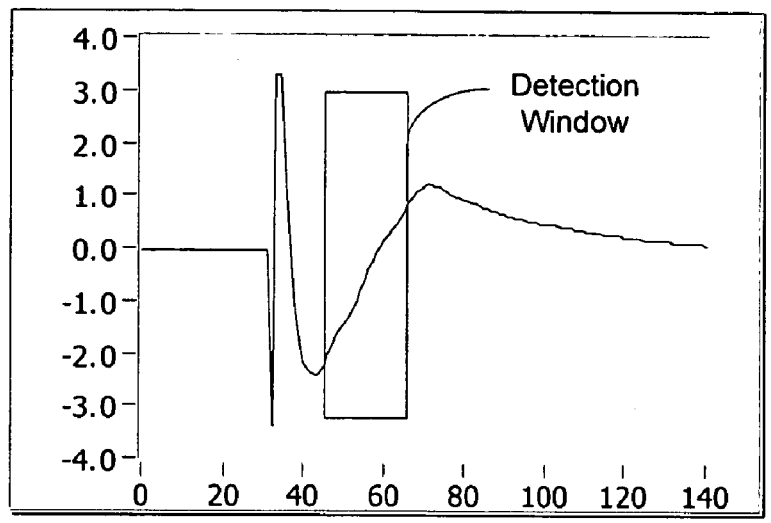
FIGS. 13A and 13B are graphs of a captured response and a pseudofusion beat, respectively.
Figure 13B:
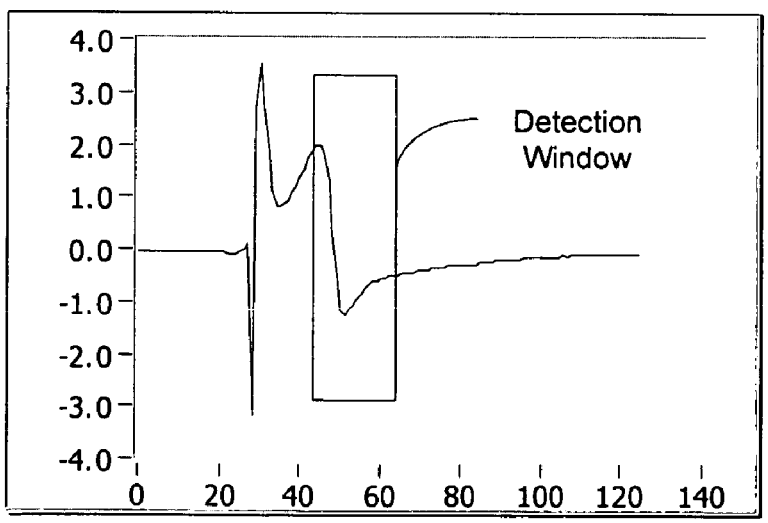

A method of detecting fusion/pseudofusion beats in accordance with the present invention relies upon canceling a template representative of a captured response from a sensed cardiac waveform and examining the resultant waveform. The resultant captured response canceled waveform for a fusion or pseudofusion beat will have a different waveform when compared to the captured response template in a fusion/pseudofusion detection window. FIGS. 13A and 13B illustrate representative waveforms of a captured response and a pseudofusion beat, respectively.

Detection of fusion/pseudofusion in accordance with a method of the present invention is illustrated with reference to the flow graph of FIG. 14. A captured response template is provided by delivering pace pulses to the heart at a voltage greater than the capture threshold. The captured response template is a waveform representative of the cardiac signal resulting from a heart contraction and includes both the pacing artifact and the evoked response. Providing a captured response template may also encompass periodically updating the captured response template. The captured response template may be periodically updated by averaging, or otherwise combining, the cardiac signal of a captured beat with the existing captured response template in accordance with the template update methods discussed above.

Figure 14:
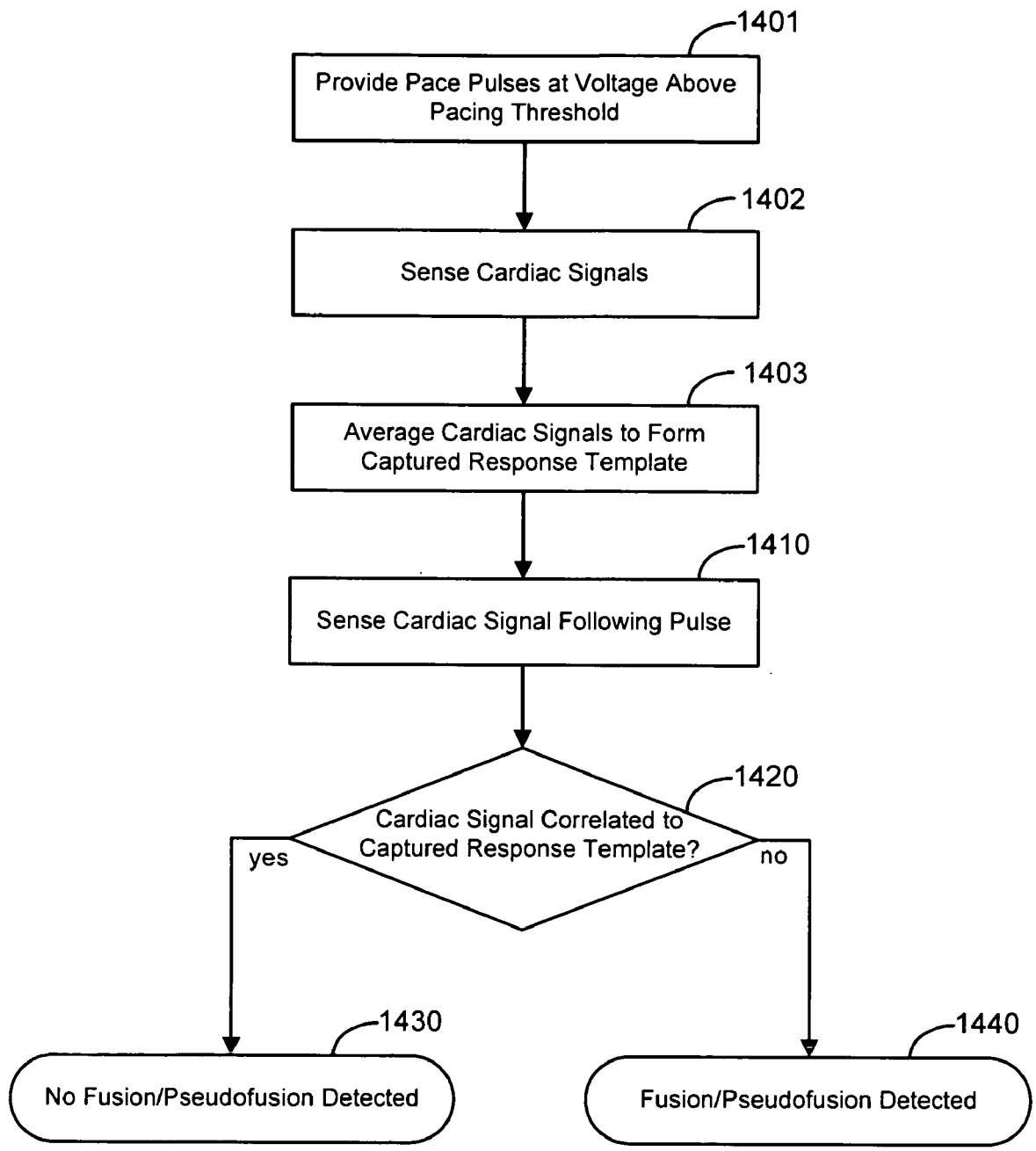
FIG. 14 is a flowchart of a method of detecting fusion/pseudofusion beats in accordance with an embodiment of the invention.

FIG. 14 illustrates a method of detecting a fusion/pseudofusion beat according to an exemplary embodiment of the invention. A captured response template is provided by the method illustrated by blocks 1401–1403. One or more pacing pulses are delivered at a voltage greater than the pacing threshold 1401 resulting in captured beats. The one or more cardiac signals of the captured beats are sensed 1402 and averaged 1403, or otherwise combined, to form the captured response template.

A cardiac signal following a pace pulse is sensed 1410. The cardiac signal is examined in a fusion/pseudofusion detection window. The fusion/pseudofusion detection window, for example, may begin at the end of a blanking period and extend for approximately 20 ms. The blanking period is a brief time interval, approximately 10 ms, following a pace pulse during which sensing is inhibited to prevent erroneous sensing of response.

If the sensed cardiac signal is correlated to the captured response template 1420 within the detection window, no fusion/pseudofusion is detected 1430. However, if the sensed cardiac signal is not correlated to the captured response template 1420, fusion/pseudofusion is detected 1440. Correlation of the sensed cardiac signal and the captured response template may be determined, for example, by calculating a correlation coefficient using the Correlated Wave Analysis technique previously discussed. If the correlation coefficient is greater than a predetermined value, for example, about 0.71, the sensed cardiac signal is considered to represent a captured response signal.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for detecting capture of a patient's heart, comprising:
   providing one or more pacing artifact templates, each pacing artifact template formed using a cardiac signal of at least one non-captured cardiac cycle;
   providing at least one template characterizing an evoked response;
   sensing a cardiac signal following a pacing pulse of a cardiac cycle, the cardiac cycle subsequent to the non-captured cardiac cycle;
   canceling a particular pacing artifact template of the one or more pacing artifact templates from the cardiac signal sensed following the pacing pulse of the subsequent cardiac cycle; and
   detecting capture of the heart for the subsequent cardiac if the pacing artifact canceled cardiac signal is correlated to the evoked response template.

2. The method of claim 1, wherein:
   providing the one or more pacing artifact templates comprises providing a number of pacing artifact templates respectively associated with a number of pacing voltages; and
   canceling the particular pacing artifact template comprises canceling a pacing artifact template associated with a pacing voltage used for the pacing pulse.

3. The method of claim 1, wherein canceling the particular pacing artifact template further comprises normalizing the particular pacing artifact template with respect to the sensed cardiac signal.

4. The method of claim 1, wherein providing the one or more pacing artifact templates further comprises updating the one or more pacing artifact templates.

5. The method of claim 1, wherein providing each of the one or more pacing artifact templates comprises:
   delivering one or more pace pulses to the heart, wherein the one or more pace pulses do not produce capture of the heart;
   sensing one or more pacing artifact waveforms produced by the one or more pulses; and
   forming the pacing artifact template using the sensed pacing artifact waveforms.

6. The method of claim 5, wherein delivering the one or more pace pulses to the heart comprises delivering the one or more pace pulses to the heart at a particular energy level.

7. The method of claim 5, wherein delivering the one or more pace pulses to the heart comprises delivering the one or more pace pulses to the heart at a particular range of energy levels.

8. The method of claim 5, wherein forming the pacing artifact template further comprises combining pacing artifact waveforms.

9. The method of claim 5, wherein sensing the one or more pacing artifact waveforms comprises sensing the pacing artifact waveforms during a capture verification window.

10. The method of claim 9, wherein the capture verification window is a time interval beginning at a first predetermined time following a pacing pulse and continuing for a second predetermined time.

11. The method of claim 10, wherein the first predetermined time is about 25 ms and the second predetermined time is about 50 ms.

12. The method of claim 1, wherein providing each of the one or more pacing artifact templates further comprises:
   delivering one or more pulses to the heart at an energy level below the capture threshold;

sensing one or more pacing artifact waveforms produced by the one or more pulses; and combining the one or more pacing artifact waveforms to form the pacing artifact template.

13. The method of claim 1, wherein providing each of the one or more pacing artifact templates further comprises:

delivering one or more pulses to the heart during a myocardial refractory period;

sensing one or more pacing artifact waveforms produced by the one or more pulses; and combining the one or more pacing artifact waveforms to form the pacing artifact template.

14. The method of claim 1, wherein providing each of the one or more pacing artifact templates comprises predicting the pacing artifact template.

15. The method of claim 1, wherein providing each of the one or more pacing artifact templates comprises predicting the pacing artifact template using a combination of one or more functions.

16. The method of claim 1, wherein providing each of the one or more pacing artifact templates comprises predicting the pacing artifact template using a combination of one or more exponential functions.

17. The method of claim 1, wherein:

the evoked response template comprises a plurality of cardiac signal features representative of an evoked response; and detecting capture of the heart comprises detecting capture if corresponding features of the pacing artifact canceled cardiac signal are correlated to the features of the evoked response template.

18. The method of claim 17, wherein canceling the particular pacing artifact template further comprises normalizing the pacing artifact template.

19. The method of claim 1, further comprising detecting loss of capture if a first predetermined number or more out of a second predetermined number of pacing artifact canceled cardiac signals are not correlated to the evoked response template.

20. The method of claim 19, wherein the first predetermined number is about 2 and the second predetermined number is about 4.

21. The method of claim 1, wherein detecting if the particular pacing artifact canceled cardiac signal is correlated to the evoked response template comprises calculating a correlation coefficient, CC, using the equation:

$$CC = \frac{\left(N\sum_{i=1}^{N} X_i Y_i - \left(\sum_{i=1}^{N} X_i\right)\left(\sum_{i=1}^{N} Y_i\right)\right)}{\sqrt{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)}}$$

where, $X_i$ represents an $i^{th}$ evoked response template sample, and $Y_i$ represents an $i^{th}$ sample of the pacing artifact canceled cardiac signal, and N represents the number of samples.

22. The method of claim 21, wherein the pacing artifact canceled cardiac signal is correlated to the evoked response template when CC is greater than about 0.71.

23. The method of claim 1, further comprising updating the evoked response template with a pacing artifact canceled cardiac signal correlated to the evoked response template.

24. The method of claim 23, wherein the evoked response template is updated using the correlated pacing artifact canceled cardiac signal in accordance with the equation:

$$U_n = B_1 C_n + B_2 S_n$$

where $U_n$ = the $n^{th}$ sample of an updated evoked response template, $C_n$ = the $n^{th}$ sample of a current evoked response template, $S_n$ = the $n^{th}$ sample of the pacing artifact canceled cardiac signal correlated to the evoked response template, and $B_1$ and $B_2$ are predetermined constants.

25. The method of claim 24, wherein $B_1$ is about 0.75 and $B_2$ is about 0.25.

26. The method of claim 1, wherein detecting capture further comprises detecting a fusion/pseudofusion beat.

27. The method of claim 1, further comprising:

providing a captured response template; and detecting a fusion/pseudofusion beat by comparing the captured response template to the sensed cardiac signal.

28. The method of claim 27, wherein detecting the fusion/pseudofusion beat comprises comparing the captured response template to the cardiac signal sensed in a fusion/pseudofusion detection window.

29. The method of claim 28, wherein the fusion/pseudofusion detection window begins at an end of a blanking period and has a length of approximately 20 ms.

30. The method of claim 27, wherein providing the captured response template comprises combining one or more captured response waveforms to form the captured response template.

31. The method of claim 27, wherein detecting the fusion/pseudofusion beat comprises determining a correlation between the sensed cardiac signal and the captured response template.

32. The method of claim 27, wherein detecting the fusion/pseudofusion beat comprises calculating a correlation coefficient between the sensed cardiac signal and the captured response template.

33. The method of 32, wherein the correlation coefficient is calculated according to the following equation:

$$CC = \frac{\left(N\sum_{i=1}^{N} X_i Y_i - \left(\sum_{i=1}^{N} X_i\right)\left(\sum_{i=1}^{N} Y_i\right)\right)}{\sqrt{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)}}$$

where, $X_i$ represents an $i^{th}$ captured response template sample, $Y_i$ represents an $i^{th}$ sample of the sensed cardiac beat, and N represents the number of samples.

34. The method of claim 32, wherein the correlation coefficient is about 0.71.

35. The method of claim 27, wherein providing the captured response template further comprises updating the captured response template using a correlated captured response.

36. The method of claim 35, wherein updating the captured response template comprises updating the captured response template using the equation $$y_n = 0.75\, y_{n-1} + 0.25 x_n$$

where $y_n$ = an updated captured response template, $y_{n-1}$ = the captured response template, and $x_n$ = the correlated captured response.

37. A method for detecting capture of a patient's heart, comprising:

providing one or more pacing artifact templates;
canceling a particular pacing artifact template of the one or more pacing artifact templates from a cardiac signal sensed following a pacing pulse; and
detecting a capture of the heart by comparing the pacing artifact cancelled cardiac signal and an evoked response reference, the evoked response reference comprising a peak-to-peak amplitude reference characterizing a peak-to-peak amplitude of an evoked response.

38. The method of claim 37, further comprising:
updating the peak-to-peak amplitude reference with a peak-to-peak amplitude of each pacing artifact canceled signal associated with the evoked response.

39. The method of claim 38, wherein the pacing artifact canceled signal is associated with the evoked response if the pacing artifact canceled signal has a peak-to-peak amplitude larger than a predetermined percentage of the peak-to-peak amplitude reference.

40. The method of claim 39, wherein the predetermined percentage is about 50%.

41. The method of claim 38, wherein updating the peak-to-peak amplitude reference comprises updating the peak-to-peak amplitude reference using the pacing artifact canceled signal if capture is detected.

42. The method of claim 38, wherein the peak-to-peak amplitude reference is updated according to the equation:

$$U = B_1 C + B_2 S$$

where U=an updated peak-to-peak amplitude reference, C=a current peak-to-peak amplitude reference, S=a peak-to-peak amplitude of the evoked response, and $B_1$ and $B_2$ are predetermined constants.

43. The method of claim 42, wherein $B_1$ is about 0.75 and $B_2$ is about 0.25.

44. The method of claim 42, wherein the updated peak-to-peak amplitude reference is constrained by an upper bound and a lower bound.

45. The method of claim 37, wherein detecting capture comprises detecting if a predetermined subset of pacing artifact canceled cardiac signals have peak-to-peak amplitudes larger than a predetermined percentage of the peak-to-peak amplitude reference.

46. The method of claim 45, wherein the predetermined subset is about 2 out of about 4, and the predetermined percentage is about 50%.

47. A medical device for detecting capture in a patient's heart, comprising:
a lead system, the lead system comprising electrodes and extending into the heart;
pulse generator circuitry coupled to the lead system, the pulse generator circuitry configured to generate pulses for stimulating the heart;
sensing circuitry, the sensing circuitry coupled to the lead system and configured to sense cardiac signals transmitted through the lead electrodes;
a control system configured to control the operation of the device; and
a capture detection system coupled to the sensing circuitry and the control systems the capture detection system comprising a template generator configured to provide one or more templates characterizing a pacing artifact, each pacing artifact template provided using a cardiac signal of a non-captured cardiac cycle, the template generator further configured to provide a template characterizing an evoked response, the capture detection system configured to cancel a particular pacing artifact template of the one or more pacing artifact templates from a cardiac signal sensed following a pacing pulse of a cardiac cycle subsequent to the non-captured cardiac cycle, and detect capture of the heart if the pacing artifact canceled cardiac signal is correlated to the evoked response template.

48. The medical device of claim 47, further comprising a switching matrix configured to connect leads from a particular heart chamber to the sensing circuitry for determining capture in the particular heart chamber.

49. The medical device of claim 47, wherein:
the pulse generator is further configured to deliver one or more pulses to the heart in such a way that the pulses do not produce a captured response;
the sensing circuitry is configured to sense pacing artifact waveforms responsive to the one or more non-captured pulses; and
the capture detection system is further configured to combine the one or more pacing artifact waveforms to form at least one of the one or more pacing artifact templates.

50. The medical device of claim 49, wherein the pulses are delivered at a voltage level below the capture threshold.

51. The medical device of claim 49, wherein the pulses are delivered during a myocardial refractory period.

52. The medical device of claim 47, wherein the capture detection system is further configured to predict the pacing artifact template.

53. The medical device of claim 52, wherein the pacing artifact template is predicted as an exponentially decaying function in a capture verification window.

54. The medical device of claim 47, wherein the capture detection system further includes circuitry configured to cancel the pacing artifact template from the sensed cardiac signal using a firmware-based implementation.

55. The medical device of claim 47, wherein the capture detection system further includes circuitry configured to cancel the pacing artifact template from the sensed cardiac signal using a hardware-based implementation.

56. The medical device of claim 55, wherein the pacing artifact template is canceled from the sensed cardiac signal by canceling an estimated pacing artifact signal generated according to the equation:

$$x(t) = A^* x(t-1),$$

where $A = e^{-T/a}$ where x(t) represents a current sample of the estimated pacing artifact signal, x(t−1) represents a previous sample of the estimated pacing artifact signal, and A is a constant derived from a time constant of the pacing artifact template, a, and a sample time, T, of the cardiac signal.

57. The medical device of claim 47, wherein:
the pulse generator circuitry is configured to deliver pulses at a voltage above a capture threshold;
the sensing circuitry is configured to sense captured cardiac waveforms produced by the pulses; and
the capture detector circuitry is configured to cancel the particular pacing artifact template from the sensed captured cardiac waveforms to form an evoked response template.

58. The medical device of claim 47, wherein the capture detection system is configured to update the evoked response template with a pacing artifact canceled cardiac signal correlated to the evoked response template.

59. The medical device of claim 47, wherein the capture detection system further comprises a fusion/pseudofusion detection system.

60. The medical device of claim 59, wherein the fusion/pseudofusion detection system is configured to provide a captured response template and detect fusion/pseudofusion by comparing the captured response template to the sensed cardiac signal.

61. A medical device for detecting capture in a patient's heart, comprising:
 a lead system, the lead system comprising electrodes and extending into the heart;
 pulse generator circuitry coupled to the lead system, the pulse generator circuitry configured to generate pulses for stimulating the heart;
 sensing circuitry, the sensing circuitry coupled to the lead system and configured to sense cardiac signals transmitted through the lead electrodes;
 a control system configured to control the operation of the device; and
 a capture detection system coupled to the sensing circuitry and the control system and configured to provide one or more pacing artifact templates characterizing a non-captured post pace signal, provide an evoked response reference comprising a peak-to-peak amplitude reference corresponding to a peak-to-peak amplitude of an evoked response and indicative of capture of the heart, cancel a particular pacing artifact template of the one or more pacing artifact templates from a cardiac signal sensed following a pulse, and detect capture of the heart by comparing the pacing artifact cancelled cardiac signal and the evoked response reference.

62. The medical device of claim 61, wherein the capture detection system is configured to detect capture when a subset of pacing artifact canceled cardiac signals have peak-to-peak amplitudes larger than a predetermined percentage of the peak-to-peak amplitude reference.

63. A system for detecting capture of a patient's heart, comprising:
 means for providing one or more pacing artifact templates, the pacing artifact template characterizing a pacing artifact signal;
 means for providing an evoked response template, the evoked response template indicative of capture of the heart;
 means for canceling a particular pacing artifact template of the one or more pacing artifact templates from a cardiac signal sensed following a pacing pulse; and
 means for detecting capture of the heart if the pacing artifact canceled cardiac signal is correlated to the evoked response template.

64. The system of claim 63, further comprising:
 means for providing a captured response template; and
 means for detecting fusion/pseudofusion using the captured response template.

* * * * *